United States Patent
Kesteleyn et al.

(10) Patent No.: US 10,206,902 B2
(45) Date of Patent: *Feb. 19, 2019

(54) MONO- OR DI-SUBSTITUTED INDOLES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Jean-François Bonfanti, Ande (FR); Tim Hugo Maria Jonckers, Heist-op-den-Berg (BE); Pierre Jean-Marie Bernard Raboisson, Rosieres (BE); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/515,563

(22) PCT Filed: Sep. 30, 2015

(86) PCT No.: PCT/EP2015/072534
§ 371 (c)(1),
(2) Date: Mar. 29, 2017

(87) PCT Pub. No.: WO2016/050831
PCT Pub. Date: Apr. 7, 2016

(65) Prior Publication Data
US 2017/0224658 A1 Aug. 10, 2017

(30) Foreign Application Priority Data
Oct. 1, 2014 (EP) .................................... 14187373
Feb. 23, 2015 (EP) .................................... 15156073

(51) Int. Cl.
*A61K 31/404* (2006.01)
*C07D 209/12* (2006.01)
*C07D 209/14* (2006.01)
*G01N 30/72* (2006.01)
*G01N 30/02* (2006.01)

(52) U.S. Cl.
CPC .......... *A61K 31/404* (2013.01); *C07D 209/12* (2013.01); *C07D 209/14* (2013.01); *G01N 30/72* (2013.01); *G01N 2030/027* (2013.01)

(58) Field of Classification Search
CPC .............................. A61K 31/404; C07D 209/12
USPC ................................... 514/415; 548/506, 511
See application file for complete search history.

(56) References Cited

U.S. PATENT DOCUMENTS

2017/0298017 A1* 10/2017 Kesteleyn ............ A61K 31/404

FOREIGN PATENT DOCUMENTS

WO WO 2013/045516 4/2013

OTHER PUBLICATIONS

International Search Report and Written Opinion dated Nov. 11, 2015, for Corresponding International Application PCT/EP2015/072534.

* cited by examiner

*Primary Examiner* — Matthew P Coughlin
*Assistant Examiner* — Sagar Patel
(74) *Attorney, Agent, or Firm* — Andrea Jo Kamage

(57) ABSTRACT

The present invention concerns mono- or di-substituted indole compounds of formula (I) which are useful to prevent or treat dengue viral infections and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

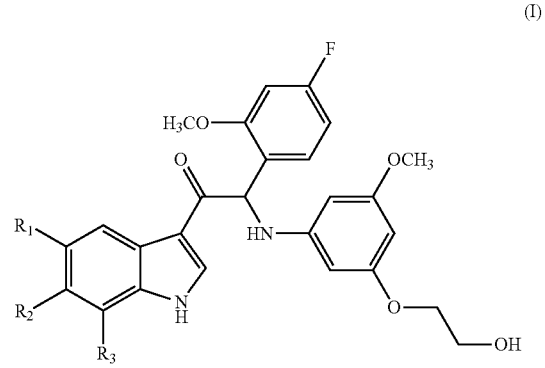

(I)

9 Claims, No Drawings
Specification includes a Sequence Listing.

SEQUENCE LISTING

<160> NUMBER OF SEQ ID NOS: 14

<210> SEQ ID NO 1
<211> LENGTH: 19
<212> TYPE: DNA
<213> ORGANISM: Dengue virus
<220> FEATURE:
<221> NAME/KEY: source
<222> LOCATION: 1..19
<223> OTHER INFORMATION: /organism="Dengue virus"
    /mol_type="unassigned DNA"

<400> SEQUENCE: 1
cggttagagg agacccctc                                                19

<210> SEQ ID NO 2
<211> LENGTH: 21

```
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 2
gagacagcag gatctctggt c                                              21

<210> SEQ ID NO 3
<211> LENGTH: 28
<212> TYPE: DNA
<213> ORGANISM: Dengue virus
<220> FEATURE:
<221> NAME/KEY: source
<222> LOCATION: 1..28
<223> OTHER INFORMATION: /organism="Dengue virus"
      /mol_type="unassigned DNA"

<400> SEQUENCE: 3
aaggactaga ggttagagga gaccccccc                                      28

<210> SEQ ID NO 4
<211> LENGTH: 18
<212> TYPE: DNA
<213> ORGANISM: Dengue virus
<220> FEATURE:
<221> NAME/KEY: source
<222> LOCATION: 1..18
<223> OTHER INFORMATION: /organism="Dengue virus"
      /mol_type="unassigned DNA"

<400> SEQUENCE: 4
ggccaggtca tcaccatt                                                  18

<210> SEQ ID NO 5
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 5
atgtccacgt cacacttcat g                                              21

<210> SEQ ID NO 6
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 6
ttccgctgcc ctgaggctct c                                              21

<210> SEQ ID NO 7
<211> LENGTH: 20
<212> TYPE: DNA
<213> ORGANISM: Dengue virus
<220> FEATURE:
<221> NAME/KEY: source
```

```
<222> LOCATION: 1..20
<223> OTHER INFORMATION: /organism="Dengue virus"
      /mol_type="unassigned DNA"

<400> SEQUENCE: 7
tcggagccgg agtttacaaa                                              20

<210> SEQ ID NO 8
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 8
tcttaacgtc cgcccatgat                                              20

<210> SEQ ID NO 9
<211> LENGTH: 19
<212> TYPE: DNA
<213> ORGANISM: Dengue virus
<220> FEATURE:
<221> NAME/KEY: source
<222> LOCATION: 1..19
<223> OTHER INFORMATION: /organism="Dengue virus"
      /mol_type="unassigned DNA"

<400> SEQUENCE: 9
attccacaca atgtggcat                                               19

<210> SEQ ID NO 10
<211> LENGTH: 23
<212> TYPE: DNA
<213> ORGANISM: Dengue virus
<220> FEATURE:
<221> NAME/KEY: source
<222> LOCATION: 1..23
<223> OTHER INFORMATION: /organism="Dengue virus"
      /mol_type="unassigned DNA"

<400> SEQUENCE: 10
ggatagacca gagatcctgc tgt                                          23

<210> SEQ ID NO 11
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 11
cattccattt tctggcgttc                                              20

<210> SEQ ID NO 12
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"
```

```
<400> SEQUENCE: 12
caatccatct tgcggcgctc                                          20

<210> SEQ ID NO 13
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 13
cagcatcatt ccaggcacag                                          20

<210> SEQ ID NO 14
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 14
caacatcaat ccaggcacag                                          20
```

MONO- OR DI-SUBSTITUTED INDOLES AS DENGUE VIRAL REPLICATION INHIBITORS

This application is a 35 U.S.C. § 371 nationalization of PCT application PCT/EP2015/072534 filed Sep. 30, 2015, which claims priority to European patent application 14187373.7 filed Oct. 1, 2014, and European patent application 15156073.7 filed Feb. 23, 2015.

The present invention relates to mono- or di-substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control the disease associated with dengue viral infection, the only available methods at present are mosquito eradication strategies to control the vector. Although progress is being made in the development of vaccines against dengue, many difficulties are encountered. These include the existence of a phenomenon referred to as antibody-dependent enhancement (ADE).

Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Despite large efforts over the past 3 decades, there is currently no vaccine available to protect humans against dengue virus disease. The main problem is to develop a vaccine that offers protection against all four serotypes (a tetravalent vaccine) to the same extent. Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

The present invention now provides compounds, mono- or di-substituted indole derivatives, which show high potent activity against all four (4) serotypes of the Dengue virus. Also the compounds according to the invention possess a good pharmacokinetic profile and surprisingly these specific compounds show an improved chiral stability.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds of formula (I)

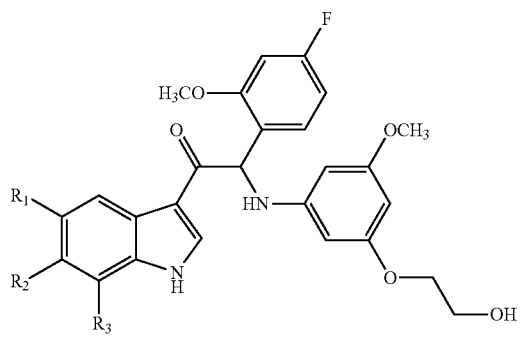

(I)

a stereo-isomeric form, a pharmaceutically acceptable salt, solvate or polymorph thereof comprising a mono- or di-substituted indole group; said compound is selected from the group wherein:

$R_1$ is H, $R_2$ is F and $R_3$ is H, F or $CH_3$;
$R_1$ is F or $CH_3$, $R_2$ is $OCH_3$ and $R_3$ is H;
$R_1$ is H, $R_2$ is Cl and $R_3$ is H or $CH_3$;
$R_1$ is F, $R_2$ is H and $R_3$ is $CH_3$;
$R_1$ is H, $R_2$ is $OCH_3$ and $R_3$ is Cl,
$R_1$ is F, $R_2$ is F and $R_3$ is H,
$R_1$ is H, $R_2$ is $OCH_3$ and $R_3$ is $CH_3$ or
$R_1$ is $CH_3$, $R_2$ is H and $R_3$ is F.

In particular the compounds of the invention or their stereo-isomeric form, a pharmaceutically acceptable salt, solvate or polymorph thereof are selected from the group:

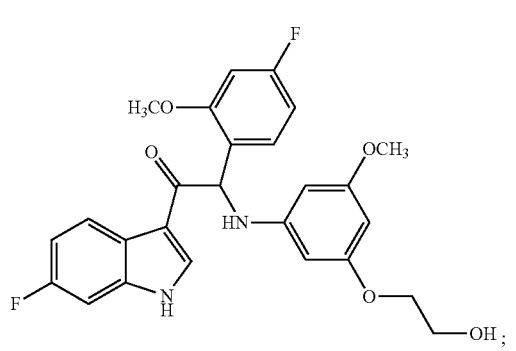

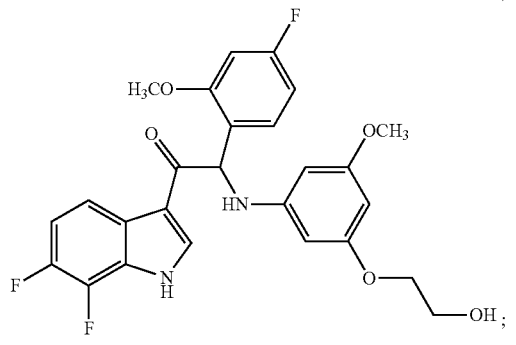

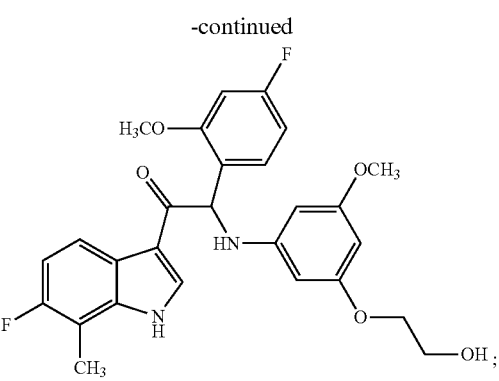

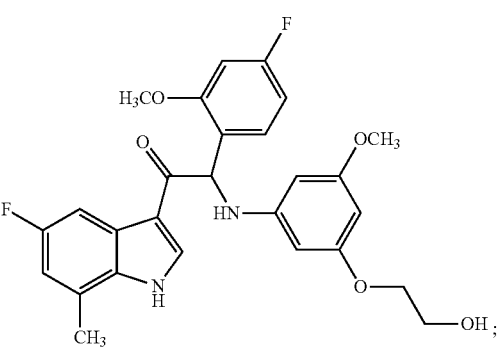

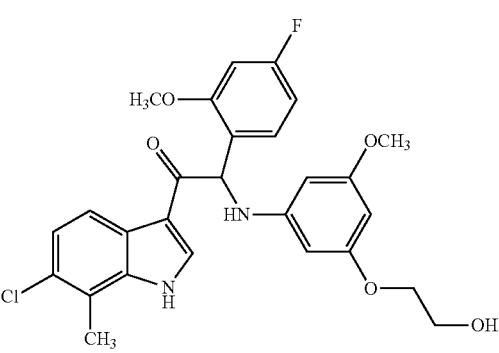

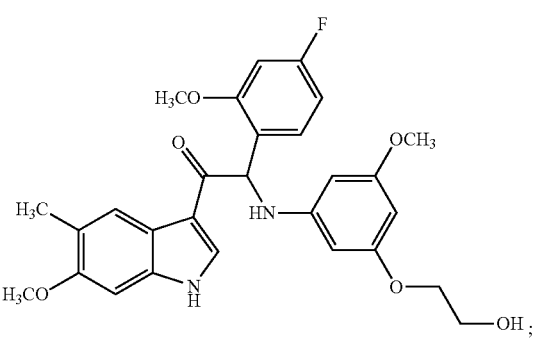

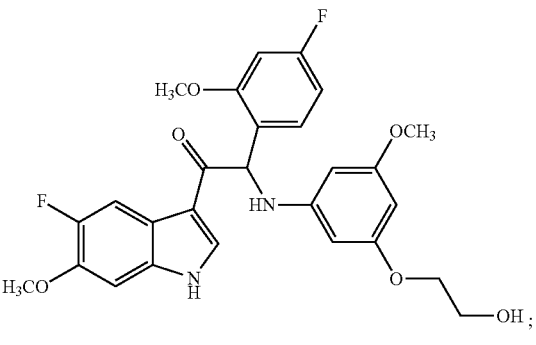

-continued

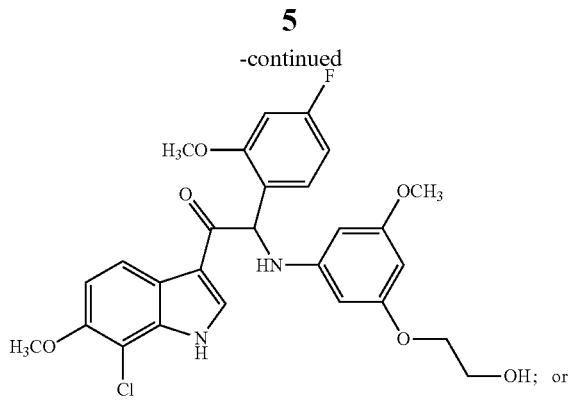

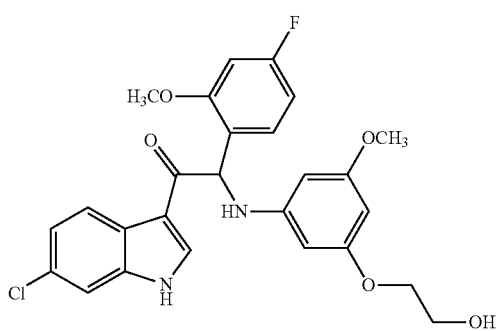

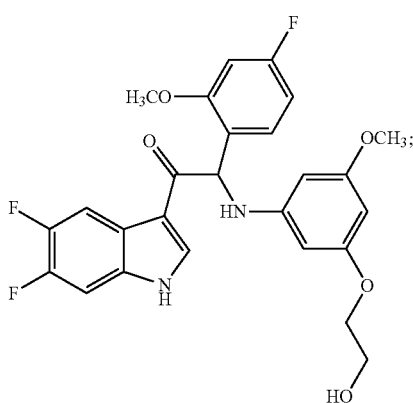

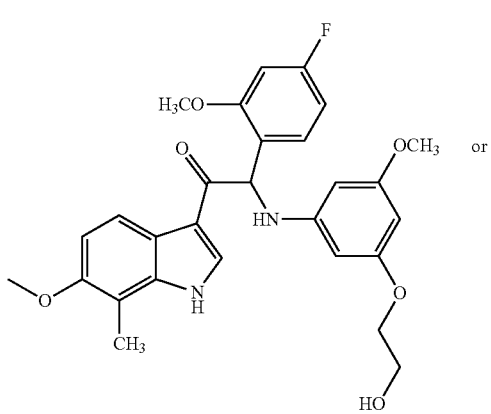

-continued

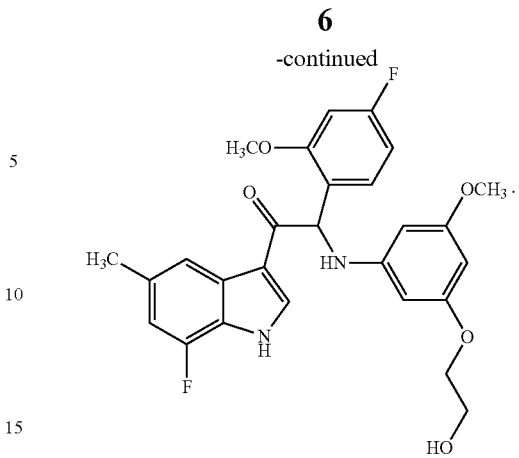

Part of the current invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in un-solvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14. The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all diastereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

General Synthetic Approaches

The synthesis of compounds of general formula I can be performed as outlined in Scheme 1. 2-(4-Fluoro-2-methoxyphenyl)acetic acid (II) can be converted to the corresponding 2-(4-fluoro-2-methoxyphenyl)acetyl chloride (III) with a chlorination reagent like for example thionyl chloride. The Friedel-Crafts reaction of the acid chloride III with a substituted indole of general formula IV can be performed using a Lewis acid reagent like for example $AlCl_3$ or $Et_2AlCl$ in a suitable solvent like for example $CH_2Cl_2$, and under suitable reaction conditions that typically involve cooling, to provide the 3-acylated indole of general formula V. The introduction of an aniline moiety in alpha position to the carbonyl moiety of the compounds of general formula V can be accomplished by a reaction sequence that involves for example bromination of V with a reagent like for example phenyltrimethylammonium tribromide in a suitable solvent like for example THF, to provide the compounds of general formula VI, and subsequent reaction of the compounds of general formula VI with 2-(3-amino-5-methoxyphenoxy)ethanol (VII) in a suitable solvent like for example $CH_3CN$, and typically using a base like for example TEA or DIPEA, to provide the compounds of general formula I as racemic mixtures. Alternatively, the compounds of general formula VI can be reacted with a O-protected aniline of general formula VIII (PG=protecting group) in a suitable solvent like for example $CH_3CN$, and typically using a base like for example TEA or DIPEA, to provide the compounds of general formula IX. A useful protecting groups is for example (but is not limited to) tert-butyl (PG=tBu). Removal of the protecting group of the compounds of general formula IX can be accomplished by methods that are familiar to those skilled in the art and include for example (but are not limited to) a reagent like for example concentrated hydrochloric acid (for PG=tBu), to provide the compounds of general formula I as racemic mixtures. Chiral separation of the compounds of general formula I can be performed by for example chiral chromatography to provide the Enantiomers A and B of general formula I.

Scheme 1
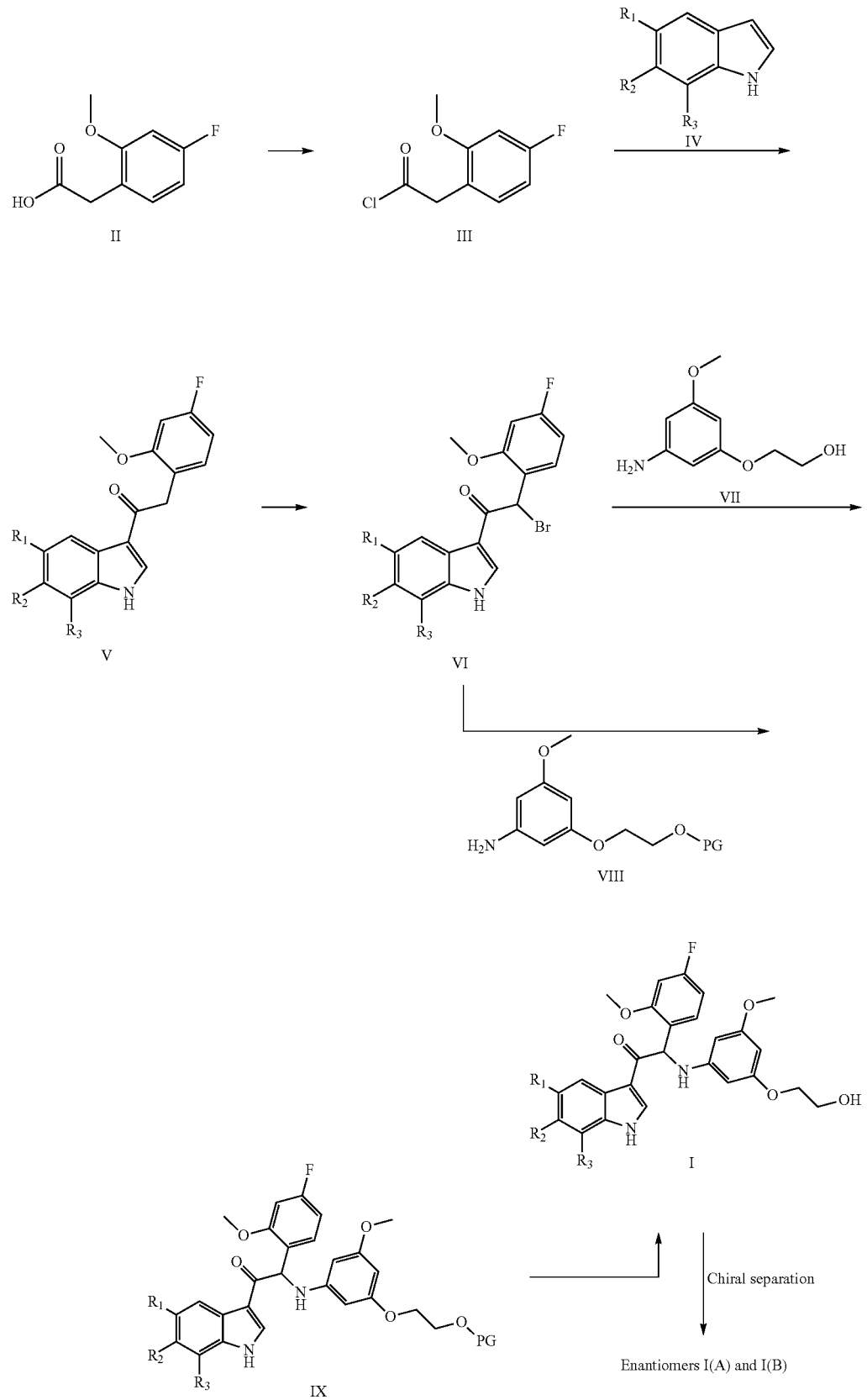

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LCMS Method codes (Flow expressed in mL/min; column temperature (T) in ° C.; Run time in minutes)

| Method code | Instrument | Column | Mobile phase | Gradient | Flow Col T | Run time (min) |
|---|---|---|---|---|---|---|
| LC-A | Waters: Acquity ® UPLC ®-DAD-SQD | Waters: BEH C18 (1.7 µm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 mL/min 55° C. | 2 |
| LC-B | Waters: Acquity ® UPLC ®-DAD-SQD | Waters: HSS T3 (1.8 µm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min 55° C. | 3.5 |
| LC-C | Waters: Acquity ® UPLC ®-DAD-Quattro Micro ™ | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-D | Dionex ®: Ultima ® 3000 ®-DAD-Brucker ® Esquire 6000 | Sunfire ® C18 (3.5 µm, 3.0 * 100 mm) with guard (3.5 µm, 3.0 * 20 mm) | A: 0.1% Formic acid in $H_2O$ B: $CH_3CN$ | 50% A for 0.20 min, to 10% A in 5.8 min, held for 4.8 min, back to 50% A in 0.20 min, held for 3.00 min. | 1.0 mL/min 30° C. | 14 |
| LC-E | Dionex ®: Ultima ® 3000 ®-DAD-Brucker ® Esquire 6000 | X-Bridge ® C18 (3.5 µm, 3.0 * 100 mm) with guard (3.5 µm, 3.0 * 20 mm) | A: 10 mM $CH_3COONH_4$ in $H_2O$ adjust pH 10 with ammonia solution B: $CH_3CN$ | 80% A for 0.20 min, to 40% A in 6.8 min, to 10% A in 1 min held for 2.8 min, back to 80% A in 0.20 min, held for 3.00 min. | 1.0 mL/min 30° C. | 14 |

SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralpak ® AD-H column (5 μm, 150 × 4.6 mm) | A: $CO_2$ B: MeOH | 30% B hold 7 min, | 3 35 | 7 100 |
| SFC-B | Daicel Chiralpak ® AD-H column (5 μm, 150 × 4.6 mm) | A: $CO_2$ B: MeOH | 40% B hold 7 min, | 3 35 | 7 100 |
| SFC-C | Daicel Chiralcel ® OJ-H column (5 μm, 250 × 4.6 mm) | A: $CO_2$ B: MeOH | 40% B hold 7 min, | 3 35 | 7 100 |
| SFC-D | Daicel Chiralcel ® OD-H column (5 μm, 150 × 4.6 mm) | A: $CO_2$ B: MeOH | 40% B hold 7 min, | 3 35 | 7 100 |
| SFC-E | Daicel Chiralcel ® OD-H column (5 μm, 150 × 4.6 mm) | A: $CO_2$ B: MeOH | 30% B hold 7 min | 3 35 | 7 100 |
| SFC-F | Daicel Chiralpak ® AS3 column (3.0 μm, 150 × 4.6 mm) | A: $CO_2$ B: EtOH + 0.2% $iPrNH_2$ + 3% $H_2O$ | 25% B hold 6 min, to 50% in 1 min hold 2.5 min | 2.5 40 | 9.5 110 |
| SFC-G | Daicel Chiralpak ® OD-H column (5.0 μm, 250 × 4.6 mm) | A: $CO_2$ B: EtOH + 0.2% $iPrNH_2$ | 35% B hold 4 min, to 50% in 1 min hold 2 min | 5 40 | 7 110 |
| SFC-H | Daicel Chiralpak ® OD3 column (3.0 μm, 150 × 4.6 mm) | A: $CO_2$ B: EtOH + 0.2% $iPrNH_2$ + 3% $H_2O$ | 40% B hold 6 min, to 50% in 1 min hold 2.5 min | 2.5 40 | 9.5 110 |
| SFC-I | Daicel Chiralpak ® AS3 column (3.0 μm, 150 × 4.6 mm) | A: $CO_2$ B: EtOH + 0.2% $iPrNH_2$ + 3% $H_2O$ | 30% B hold 6 min, to 50% in 1 min hold 2.5 min | 2.5 40 | 9.5 110 |
| SFC-J | Daicel Chiralpak ® OD-H column (5.0 μm, 250 × 4.6 mm) | A: $CO_2$ B: EtOH + 0.2% $iPrNH_2$ | 30% B hold 4 min, to 50% in 1 min hold 2 min | 5 40 | 7 110 |
| SFC-K | Daicel Chiralpak ® OD3 column (3.0 μm, 150 × 4.6 mm) | A: $CO_2$ B: MeOH + 0.2% $iPrNH_2$ + 3% $H_2O$ | 35% B hold 6 min, to 50% in 1 min hold 2.5 min | 2.5 40 | 9.5 110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: $[\alpha]°$ ($\lambda$, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1: Synthesis of 1-(6-fluoro-1H-indol-3-yl)-2-(4-fluoro-2-methoxyphenyl)-2-((3-(2-hydroxyethoxy)-5-methoxyphenyl)amino)ethanone (Compound 1) and Chiral Separation into Enantiomers 1A and 1B

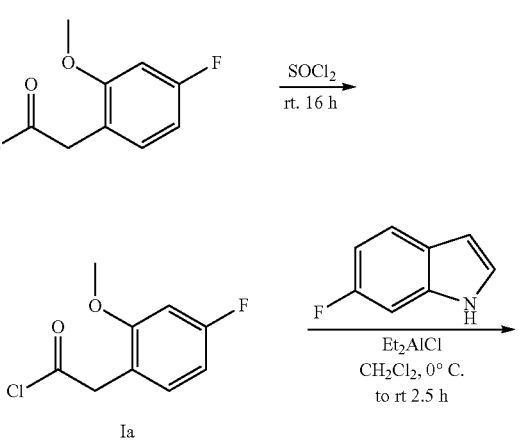

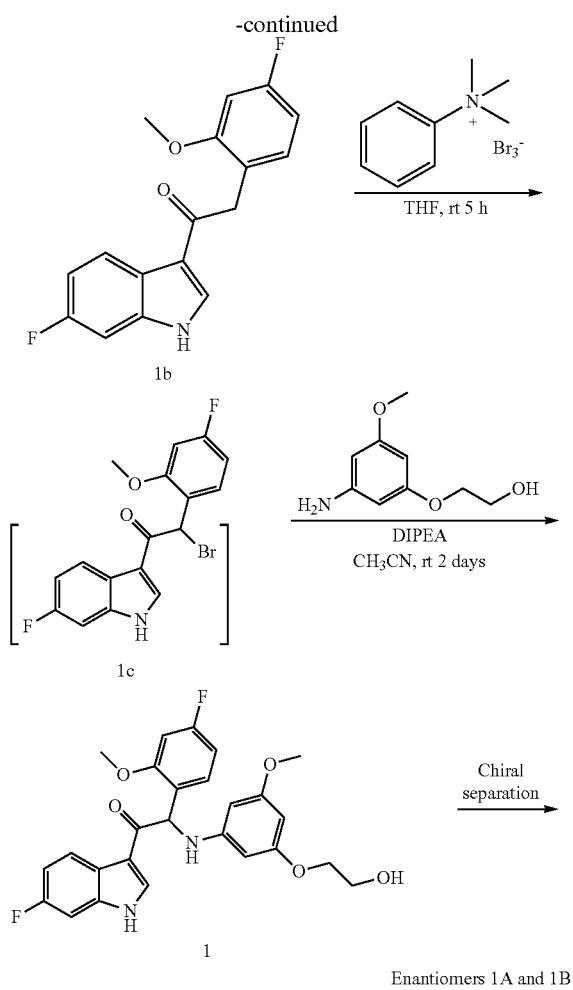

Enantiomers 1A and 1B

Synthesis of Intermediate 1a:

2-(4-Fluoro-2-methoxyphenyl)acetic acid [CAS 886498-61-9] (28.9 g, 157 mmol) was added in small portions to thionyl chloride (150 mL) and the resulting solution was stirred overnight at room temperature. The solvent was concentrated under reduced pressure and co-evaporated with toluene to give 2-(4-fluoro-2-methoxyphenyl)acetyl chloride 1a (31.8 g) as an oily residue that was used without further purification in the next step.

Synthesis of Intermediate 1b:

A solution of 6-fluoro-1H-indole [CAS 399-51-9] (14.2 g, 105 mmol) in $CH_2Cl_2$ (400 mL) was cooled to 0° C. under $N_2$-atmosphere. A solution of diethylaluminum chloride 1M in hexane (160 mL, 160 mmol) was added over a period of 10 min to the stirred solution and the resulting mixture was kept at 0° C. for 40 min. Then, a solution of 2-(4-fluoro-2-methoxyphenyl)acetyl chloride 1a (31.8 g, 160 mmol) in $CH_2Cl_2$ (300 mL) was added dropwise over a period of 2.5 h while keeping the internal temperature of the reaction mixture below 5° C. The temperature of the stirred reaction mixture was maintained at 0° C. for 3.5 h. The ice-bath was removed and after stirring at room temperature for 2.5 h, the reaction mixture was cooled again to 0° C. and the reaction was quenched by the slow addition of a solution of potassium sodium tartrate tetrahydrate (Rochelle salt) [CAS 6100-16-9] (59.6 g, 210 mmol) in water (70 mL) while keeping the internal temperature of the mixture below 10° C. After stirring for an additional 30 min at 0° C., the ice-bath was removed and the resulting mixture was diluted with THF (1 L). $Na_2SO_4$ (150 g) was added and after overnight stirring, the mixture was filtered over Dicalite®. The filter cake was washed twice with THF (2×1 L). The combined filtrates were evaporated under reduced pressure to a residual volume of approximately 50 mL. A white precipitate was filtered off and dried under vacuum at 50° C. to provide 1-(6-fluoro-1H-indol-3-yl)-2-(4-fluoro-2-methoxyphenyl)ethanone 1b (22.3 g) as a white powder.

Synthesis of Compound 1 and Chiral Separation of Enantiomers 1A and 1B:

A stirred solution of 1-(6-fluoro-1H-indol-3-yl)-2-(4-fluoro-2-methoxyphenyl)-ethanone 1b (11.0 g, 36.5 mmol) in THF (300 mL) was cooled to 0° C. under $N_2$-atmosphere. A solution of phenyltrimethylammonium tribromide [CAS 4207-56-1] (13.9 g, 36.9 mmol) in THF (100 mL) was added dropwise over a period of 45 min. The resulting suspension was stirred at room temperature for 5 h and evaporated under reduced pressure to a white residue. This residue, containing the crude 2-bromo-1-(6-fluoro-1H-indol-3-yl)-2-(4-fluoro-2-methoxy-phenyl)ethanone 1c, was dissolved in acetonitrile (300 mL) and the mixture was stirred at room temperature. After addition of 2-(3-amino-5-methoxy-phenoxy)ethanol [CAS 725237-16-1] (13.4 g, 73 mmol) and diisopropylethylamine (12.6 mL, 73 mmol), the mixture was stirred at room temperature for two days—until complete conversion to Compound 1. The reaction mixture was poured out into water (1.5 L) and extracted with 2-methyl-THF (2×750 mL). The combined extracts were washed with 0.5N HCl (800 mL), a saturated aqueous solution of $NaHCO_3$ (200 mL) and brine (200 mL), dried over $MgSO_4$ and evaporated under reduced pressure. The oily residue was purified by Preparative HPLC (Stationary phase: RP Uptisphere® Prep C18 ODB—10 μm, 30×150 mm, Mobile phase: 0.25% $NH_4HCO_3$ solution in water, $CH_3CN$). The product fractions were concentrated, dissolved in methanol and concentrated again yielding 1-(6-fluoro-1H-indol-3-yl)-2-(4-fluoro-2-methoxyphenyl)-2-((3-(2-hydroxyethoxy)-5-methoxyphenyl)amino)ethanone (Compound 1, 9.3 g) as a racemic mixture.

Chiral separation of the enantiomers of Compound 1 (9.3 g) was performed via Normal Phase Chiral HPLC (Stationary phase: AS 20 μm (1 kg), Mobile phase: 100% MeOH). The product fractions were combined and evaporated to provide Enantiomer 1A (4.5 g) as the first eluted product and Enantiomer 1B (4.6 g) as the second eluted product. Both enantiomers 1A and 1B occurred as sticky oils. Enantiomer 1A (4.5 g) was precipitated from a solution in MeOH (20 mL) by slow addition of water (11 mL). After stirring for 30 min at room temperature a white solid was filtered off, washed with small quantities of a MeOH/water (1/1) mixtures and dried under vacuum at 50° C. to provide Enantiomer 1A (2.4 g) as an amorphous white powder. Enantiomer 1B (4.6 g) was solidified by trituration of the oily residue with a mixture of MeOH (10 mL) and water (15 mL) under vigorous stirring for 25 min. The solids were filtered off and subsequently crystallized from a mixture of MeOH (70 mL) and water (30 mL) under stirring at room temperature for 3 h. A white precipitate was filtered off and dried under vacuum at 50° C. to provide Enantiomer 1B (2.50 g) as an amorphous white powder.

Compound 1:

$^1$H NMR (360 MHz, DMSO-$d_6$) δ ppm 3.64 (q, J=4.9 Hz, 2H), 3.61 (s, 3H), 3.76-3.90 (m, 2H), 3.96 (s, 3H), 4.80 (t, J=5.3 Hz, 1H), 5.72 (t, J=2.2 Hz, 1H), 5.94 (d, J=2.2 Hz, 2H), 6.14 (d, J=8.0 Hz, 1H), 6.38 (d, J=8.1 Hz, 1H), 6.73 (td, J=8.4, 2.6 Hz, 1H), 6.93 (dd, J=11.5, 2.4 Hz, 1H), 7.06 (ddd, J=9.7, 8.8, 2.4 Hz, 1H), 7.27 (dd, J=9.5, 2.2 Hz, 1H), 7.37 (dd, J=8.6, 6.8 Hz, 1H), 8.15 (dd, J=8.8, 5.9 Hz, 1H), 8.43 (s, 1H), 12.07 (br. s, 1H) LC/MS (method LC-B): $R_t$ 1.86 min, MH$^+$ 483

Enantiomer 1A:

$^1$H NMR (360 MHz, DMSO-d$_6$) δ ppm 3.60 (s, 3H) 3.64 (m, J=6.60 Hz, 2H) 3.73-3.90 (m, 2H) 3.95 (s, 3H) 4.80 (t, J=4.94 Hz, 1H) 5.71 (br. s., 1H) 5.93 (br. s, 2H) 6.14 (d, J=7.95 Hz, 1H) 6.38 (d, J=7.97 Hz, 1H) 6.73 (t, J=8.41 Hz, 1H) 6.93 (d, J=11.24 Hz, 1H) 7.05 (t, J=9.02 Hz, 1H) 7.27 (d, J=9.58 Hz, 1H) 7.37 (t, J=7.70 Hz, 1H) 8.09-8.19 (m, 1H) 8.43 (s, 1H) 12.06 (s, 1H)

LC/MS (method LC-A): $R_t$ 1.03 min, MH$^+$ 483

$[α]_D^{20}$: +96.9° (c 0.389, DMF)

Chiral SFC (method SFC-F): $R_t$ 1.73 min, MH$^+$ 483, chiral purity 100%.

Enantiomer 1B:

$^1$H NMR (400 MHz, DMSO-d$_6$) δ ppm 3.61 (s, 3H) 3.64 (t, J=5.12 Hz, 2H) 3.76-3.89 (m, 2H) 3.95 (s, 3H) 4.77 (br. s, 1H) 5.71 (t, J=2.01 Hz, 1H) 5.94 (d, J=2.11 Hz, 2H) 6.14 (d, J=7.97 Hz, 1H) 6.35 (d, J=8.00 Hz, 1H) 6.72 (td, J=8.49, 2.44 Hz, 1H) 6.92 (dd, J=11.36, 2.48 Hz, 1H) 7.05 (td, J=9.29, 2.38 Hz, 1H) 7.26 (d, J=9.49 Hz, 1H) 7.37 (dd, J=8.58, 6.88 Hz, 1H) 8.14 (dd, J=8.77, 5.59 Hz, 1H) 8.42 (s, 1H) 12.08 (br. s., 1H)

LC/MS (method LC-A): $R_t$ 1.03 min, MH$^+$ 483

$[α]_D^{20}$: −100.0° (c 0.478, DMF)

Chiral SFC (method SFC-F): $R_t$ 2.38 min, MH$^+$ 483, chiral purity 100%.

Example 1.1: Chiral Stability of Enantiomer 1A at pH 7.4

The chiral stability of Enantiomer 1A (R=OMe) was evaluated by determination of the enantiomeric excess (ee %) after incubation for 24 h and 48 h in a buffered solution at pH 7.4 at 40° C. and 60° C. To assess the influence of the methoxy-substituent of Enantiomer 1A (R=OMe) on the stability against racemization, the chiral stability of Enantiomer 1'A (R=H) was tested under the same conditions.

To this end, 5 μM buffered (pH=7.4) solutions of 1A and 1'A were prepared by mixing 25 μL of a 100 μM solution of 1A or 1'A in DMSO with 475 μL aqueous buffer pH 7.4. Samples were taken 24 h and 48 h after incubation at 40° C. and 60° C. The analytical samples were analyzed by Chiral SFC (MS detection) and the chiral purity was expressed as the enantiomeric excess (ee %=% enantiomer A−% enantiomer B). Both Enantiomers 1A and 1'A had a chiral purity of 100% prior to their incubation.

|  |  | ee% Sampling timepoints (h) | |
|---|---|---|---|
| Compound | Temperature | 24 | 48 |
| 1A | 40° C. | 100 | 100 |
|  | 60° C. | 100 | 96 |
| 1'A | 40° C. | 92 | 84 |
|  | 60° C. | 26 | 9 |

Example 2: synthesis 2-(4-fluoro-2-methoxyphenyl)-1-(6-fluoro-7-methyl-1H-indol-3-yl)-2-((3-(2-hydroxyethoxy)-5-methoxyphenyl)amino)ethanone (Compound 2) and Chiral Separation into Enantiomers 2A and 2B

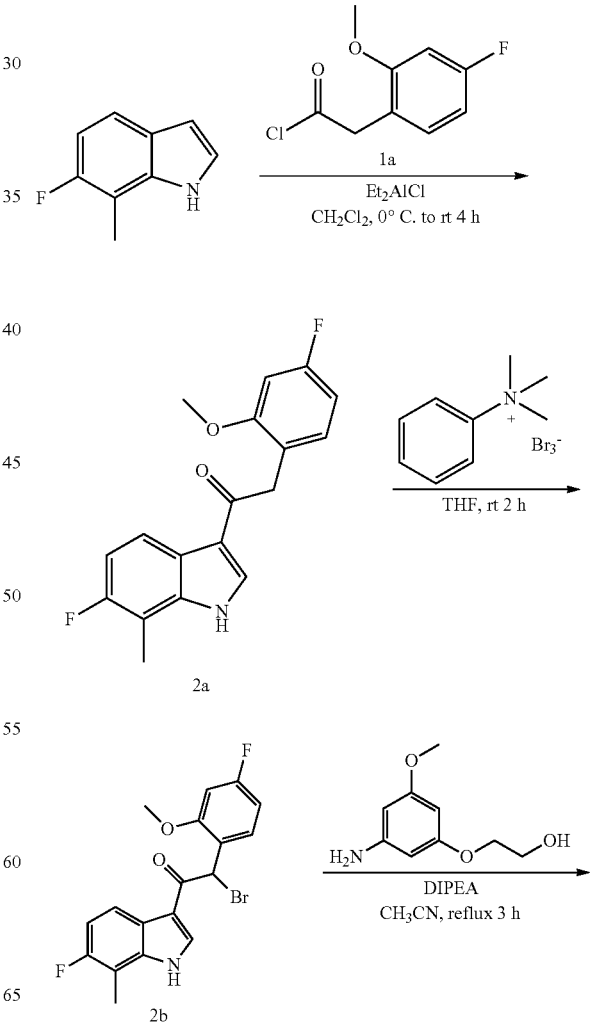

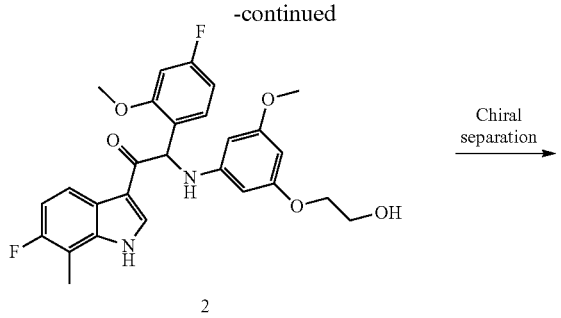

2

Enantiomers 2A and 2B

Synthesis of Intermediate 2a:

A stirred solution of 6-fluoro-7-methyl-1H-indole [CAS 57817-10-4] (5.41 g, 36.2 mmol) in CH$_2$Cl$_2$ (100 mL) was cooled on ice under N$_2$-atmosphere. A solution of diethylaluminum chloride 1M in hexane (54.4 mL, 54.4 mmol) was added dropwise. After 15 min at 0° C., a solution of 2-(4-fluoro-2-methoxyphenyl)acetyl chloride 1a (11.0 g, 54.4 mmol, for synthesis: see Example 1) in CH$_2$Cl$_2$ (30 mL) was added dropwise while keeping the internal temperature below 5° C. The ice-bath was removed and the resulting suspension was stirred at room temperature for 4 h. The reaction mixture was poured out slowly into a cooled (0° C.) saturated aqueous solution of NaHCO$_3$. The mixture was filtered over Dicalite® and the filter cake was washed with THF. The combined filtrates were extracted with EtOAc, dried over MgSO$_4$ and evaporated under reduced pressure. The residue was triturated with CH$_2$Cl$_2$ and the solids were filtered off to give 2-(4-fluoro-2-methoxyphenyl)-1-(6-fluoro-7-methyl-1H-indol-3-yl)-ethanone 2a (7.47 g) as a white powder.

Synthesis of Intermediate 2b:

A stirred solution of 2-(4-fluoro-2-methoxyphenyl)-1-(6-fluoro-7-methyl-1H-indol-3-yl)ethanone 2a (7.43 g, 23.56 mmol) in THF (100 mL) was cooled at 0° C. under N$_2$-atmosphere. A solution of phenyltrimethylammonium tribromide [CAS 4207-56-1] (8.96 g, 23.8 mmol) in THF (100 mL) was added dropwise. After the addition, the reaction mixture was stirred for 2 h at room temperature.

The suspension was filtered to remove the solids and the filtrate was evaporated under reduced pressure. The residue was triturated with CH$_2$Cl$_2$, the solids were filtered off and dried under vacuum to provide 2-bromo-2-(4-fluoro-2-methoxyphenyl)-1-(6-fluoro-7-methyl-1H-indol-3-yl)ethanone 2b (8.95 g).

Synthesis of Compound 2 and Chiral Separation of Enantiomers 2A and 2B:

A mixture of 2-bromo-2-(4-fluoro-2-methoxyphenyl)-1-(6-fluoro-7-methyl-1H-indol-3-yl)ethanone 2b (3.30 g, 8.38 mmol), 2-(3-amino-5-methoxyphenoxy)ethanol [CAS 725237-16-1] (1.54 g, 8.38 mmol), and diisopropylethylamine (1.44 mL, 8.38 mmol) were mixed in CH$_3$CN (100 mL) and the mixture was heated under reflux for 3 h. After cooling to room temperature, the solvent was evaporated under reduced pressure and the residue was purified by column chromatography on silica (Stationary phase: HP-Spher 25 µm (340 g), Mobile phase: heptane/EtOAc gradient: 100/0 to 0/100). The product fractions were concentrated and subsequently purified by Preparative HPLC (Stationary phase: Uptisphere® C18 ODB-10 µm, 200 g, 5 cm, Mobile phase: 0.25% NH$_4$HCO$_3$ solution in water, CH$_3$CN). The product fractions were concentrated, dissolved in methanol and concentrated again to provide 2-(4-fluoro-2-methoxyphenyl)-1-(6-fluoro-7-methyl-1H-indol-3-yl)-2-((3-(2-hydroxyethoxy)-5-methoxyphenyl)amino) ethanone (Compound 2, 1.4 g) as a racemic mixture.

Chiral separation of the enantiomers of Compound 2 (1.18 g) was performed via Preparative SFC (Stationary phase: Chiralcel® Diacel® OD 20×250 mm, Mobile phase: CO$_2$, EtOH with 0.2% iPrNH$_2$) and evaporation of the product fractions under reduced pressure. The first eluted enantiomer was isolated as the hydrochloric acid salt by precipitation from a mixture of MeOH (30 mL), 1N HCl (5 mL) and water (130 mL). A white precipitate was formed after overnight stirring and was filtered off and dried in vacuum at room temperature to provide 328 mg of enantiomer 2A (as the hydrochloric acid salt). The second eluted enantiomer was solidified by lyophilization from a mixture of CH$_3$CN/water to give 385 mg of enantiomer 2B as an amorphous powder.

Compound 2:

$^1$H NMR (360 MHz, DMSO-d$_6$) δ ppm 2.38 (d, J=1.62 Hz, 3H) 3.61 (s, 3H) 3.64 (q, J=5.12 Hz, 2H) 3.76-3.89 (m, 2H) 3.96 (s, 3H) 4.79 (t, J=5.54 Hz, 1H) 5.71 (t, J=2.11 Hz, 1H) 5.95 (d, J=2.13 Hz, 2H) 6.16 (d, J=7.95 Hz, 1H) 6.36 (d, J=7.96 Hz, 1H) 6.72 (td, J=8.49, 2.47 Hz, 1H) 6.93 (dd, J=11.37, 2.49 Hz, 1H) 7.01 (dd, J=10.29, 8.71 Hz, 1H) 7.37 (dd, J=8.62, 6.85 Hz, 1H) 7.96 (dd, J=8.73, 5.18 Hz, 1H) 8.43 (s, 1H) 12.19 (s, 1H)

LC/MS (method LC-A): R$_t$ 1.08 min, MH$^+$ 497

Enantiomer 2A:

$^1$H NMR (360 MHz, DMSO-d$_6$) δ ppm 2.38 (d, J=0.22 Hz, 3H) 3.61 (s, 3H) 3.64 (t, J=5.21 Hz, 2H) 3.83 (qt, J=10.02, 5.27 Hz, 2H) 3.96 (s, 3H) 5.71 (t, J=1.46 Hz, 1H) 5.95 (d, J=2.11 Hz, 2H) 6.16 (br. s., 1H) 6.36 (br. s, 1H) 6.72 (td, J=8.55, 2.62 Hz, 1H) 6.93 (dd, J=11.33, 2.46 Hz, 1H) 7.01 (t, J=9.49 Hz, 1H) 7.37 (dd, J=8.64, 6.90 Hz, 1H) 7.96 (dd, J=8.73, 5.39 Hz, 1H) 8.43 (d, J=3.24 Hz, 1H) 12.19 (d, J=2.95 Hz, 1H)

LC/MS (method LC-A): R$_t$ 1.08 min, MH$^+$ 497

[α]$_D^{20}$: −82.7° (c 0.5055, DMF)

Chiral SFC (method SFC-G): R$_t$ 1.69 min, MH$^+$ 497, chiral purity 100%.

CHN analysis: Anal. Calcd for C$_{27}$H$_{26}$F$_2$N$_2$O$_5$.HCl: C, 60.85; H, 5.11; N, 5.26.

Found: C, 62.83; H, 5.02; N, 5.36.

Enantiomer 2B:

$^1$H NMR (360 MHz, DMSO-d$_6$) δ ppm 2.38 (d, J=1.62 Hz, 3H) 3.61 (s, 3H) 3.64 (q, J=5.43 Hz, 2H) 3.75-3.89 (m, 2H) 3.96 (s, 3H) 4.79 (t, J=5.58 Hz, 1H) 5.71 (t, J=2.11 Hz, 1H) 5.95 (d, J=2.20 Hz, 2H) 6.16 (d, J=7.97 Hz, 1H) 6.36 (d, J=8.00 Hz, 1H) 6.72 (td, J=8.56, 2.56 Hz, 1H) 6.93 (dd, J=11.37, 2.49 Hz, 1H) 7.01 (dd, J=10.29, 8.72 Hz, 1H) 7.37 (dd, J=8.68, 6.89 Hz, 1H) 7.96 (dd, J=8.75, 5.21 Hz, 1H) 8.43 (s, 1H) 12.19 (br. s., 1H)

LC/MS (method LC-A): R$_t$ 1.09 min, MH$^+$ 497

[α]$_D^{20}$: +86.7° (c 0.5075, DMF)

Chiral SFC (method SFC-G): R$_t$ 2.88 min, MH$^+$ 497, chiral purity 100%.

Example 3: Synthesis of 1-(6-chloro-7-methyl-1H-indol-3-yl)-2-(4-fluoro-2-methoxyphenyl)-2-((3-(2-hydroxyethoxy)-5-methoxyphenyl)amino)ethanone (Compound 3) and Chiral Separation into Enantiomers 3A and 3B

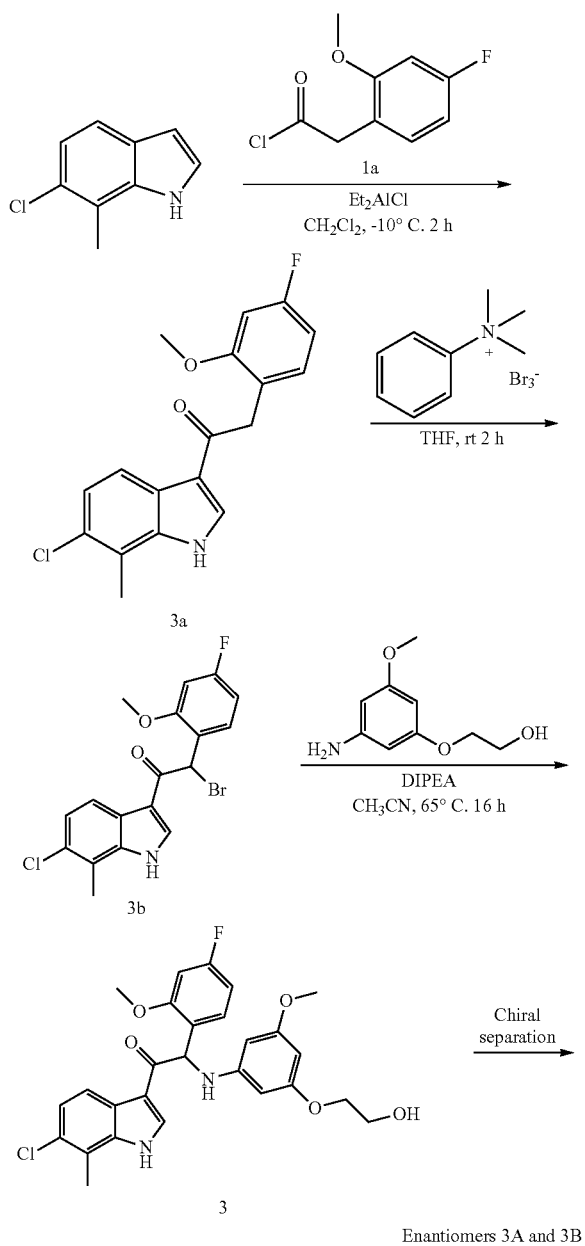

Enantiomers 3A and 3B

Synthesis of Intermediate 3a:

A stirred solution of 6-chloro-7-methyl-1H-indole [CAS 57817-09-1] (3.2 g, 19.3 mmol) in CH$_2$Cl$_2$ (150 mL) under N$_2$-flow, was cooled on an ice-NaCl cooling bath. Diethylaluminum chloride 1M in hexane (29 mL, 29 mmol) was added over a period of 2 min and the cooled solution was stirred at −10° C. for 30 min. A solution of 2-(4-fluoro-2-methoxyphenyl)acetyl chloride 1a (5.48 g, 27.1 mmol, synthesis: see Example 1) in CH$_2$Cl$_2$ (30 mL) was added dropwise over 30 min while keeping the internal temperature below −10° C. and the resulting mixture was stirred for an additional 2 h at −10° C. The reaction was quenched by the slow addition of a solution of potassium sodium tartrate tetrahydrate (Rochelle salt) [CAS 6100-16-9] (10.9 g, 38.6 mmol) in water (10 mL) and the mixture was stirred at room temperature for 15 min. A white precipitate was present in the reaction mixture. The precipitate was isolated by filtration, washed with water and dried under vacuum to provide 1-(6-chloro-7-methyl-1H-indol-3-yl)-2-(4-fluoro-2-methoxyphenyl)ethanone 3a (4200 mg) as an off-white solid.

Synthesis of Intermediate 3b:

A solution of 1-(6-chloro-7-methyl-1H-indol-3-yl)-2-(4-fluoro-2-methoxyphenyl)-ethanone 3a (2000 mg, 6.03 mmol) in THF (120 mL) was stirred at room temperature under N$_2$-atmosphere. A solution of phenyltrimethylammonium tribromide [CAS 4207-56-1] (2.38 g, 6.33 mmol) in THF (35 mL) was added dropwise and the mixture was stirred for an additional 90 min at room temperature. The precipitate was filtered off and the filtrate was concentrated under vacuum to provide 2-bromo-1-(6-chloro-7-methyl-1H-indol-3-yl)-2-(4-fluoro-2-methoxyphenyl)ethanone 3b (2200 mg) as an off-white powder.

Synthesis of Compound 3 and Chiral Separation of Enantiomers 3A and 3B:

2-Bromo-1-(6-chloro-7-methyl-1H-indol-3-yl)-2-(4-fluoro-2-methoxyphenyl)-ethanone 3b (1.31 g, 2.23 mmol) was suspended in CH$_3$CN (60 mL). 2-(3-Amino-5-methoxyphenoxy)ethanol [CAS 725237-16-1] (0.6 g, 2.46 mmol), and diisopropylethylamine (847 µL, 4.91 mmol) were added and the stirred mixture was heated at 65° C. overnight. The mixture was concentrated in vacuum and the residue was partitioned between EtOAc and water. The organic layer was separated, dried over Na$_2$SO$_4$, filtered and evaporated under reduced pressure. The residue was purified via Preparative HPLC (Stationary phase: Uptisphere® C18 ODB-10 µm, 200 g, 5 cm, Mobile phase: 0.25% NH$_4$HCO$_3$ solution in water, CH$_3$CN) to give 1-(6-chloro-7-methyl-1H-indol-3-yl)-2-(4-fluoro-2-methoxyphenyl)-2-((3-(2-hydroxyethoxy)-5-methoxyphenyl)amino)ethanone (Compound 3, 590 mg) as a racemic mixture.

Chiral separation of the enantiomers of Compound 3 (560 mg) was performed using Normal Phase Chiral separation (Stationary phase: AS 5 µm, Mobile phase: 100% MeOH, isocratic elution. Detection wavelength 308 nm, flow 1 mL/min). The product fractions were combined and evaporated to provide Enantiomer 3A as the first eluted product and Enantiomer 3B as the second eluted product. Both enantiomers 3A and 3B occurred as sticky oils. The Enantiomers were dissolved in a MeOH/CH$_2$Cl$_2$ (1/1) mixture and evaporated under reduced pressure to provide Enantiomer 3A (245 mg) and Enantiomer 3B (263 mg) as amorphous powders.

Compound 3:

$^1$H NMR (400 MHz, CHLOROFORM-d) δ ppm 2.48 (s, 3H) 3.70 (s, 3H) 3.88-3.92 (m, 2H) 3.93-4.02 (m, 2H) 4.03 (s, 3H) 5.55 (br. s, 1H) 5.83 (t, J=2.20 Hz, 1H) 5.89 (d, J=2.16 Hz, 2H) 6.12 (s, 1H) 6.54-6.66 (m, 2H) 7.28 (d, J=7.80 Hz, 1H) 7.33 (dd, J=8.55, 6.60 Hz, 1H) 8.12-8.17 (m, 2H) 8.59 (br. s., 1H)

LC/MS (method LC-B): R$_t$ 2.08 min, MH$^+$ 513

Enantiomer 3A:

$^1$H NMR (400 MHz, DMSO-d$_6$) δ ppm 2.50 (s, 3H) 3.61 (s, 3H) 3.64 (q, J=5.54 Hz, 2H) 3.77-3.90 (m, 2H) 3.96 (s, 3H) 4.78 (t, J=5.40 Hz, 1H) 5.71 (t, J=2.12 Hz, 1H) 5.95 (d, J=2.13 Hz, 2H) 6.17 (d, J=7.96 Hz, 1H) 6.35 (d, J=7.96 Hz, 1H) 6.72 (td, J=8.48, 2.49 Hz, 1H) 6.93 (dd, J=11.35, 2.50

Hz, 1H) 7.21 (d, J=8.61 Hz, 1H) 7.37 (dd, J=8.60, 6.87 Hz, 1H) 7.98 (d, J=8.50 Hz, 1H) 8.44 (s, 1H) 12.23 (s, 1H)

LC/MS (method LC-A): $R_t$ 1.12 min, $MH^+$ 513

$[\alpha]_D^{20}$: +95.2° (c 0.605, DMF)

Chiral SFC (method SFC-H): $R_t$ 3.21 min, $MH^+$ 513, chiral purity 100%.

Enantiomer 3B:

$^1$H NMR (400 MHz, DMSO-$d_6$) δ ppm 2.50 (s, 3H) 3.61 (s, 3H) 3.64 (q, J=5.38 Hz, 2H) 3.76-3.90 (m, 2H) 3.96 (s, 3H) 4.77 (t, J=5.51 Hz, 1H) 5.71 (t, J=2.12 Hz, 1H) 5.95 (d, J=2.13 Hz, 2H) 6.16 (d, J=7.96 Hz, 1H) 6.35 (d, J=7.96 Hz, 1H) 6.72 (td, J=8.48, 2.49 Hz, 1H) 6.93 (dd, J=11.35, 2.49

Hz, 1H) 7.21 (d, J=8.51 Hz, 1H) 7.37 (dd, J=8.60, 6.87 Hz, 1H) 7.98 (d, J=8.50 Hz, 1H) 8.44 (s, 1H) 12.23 (s, 1H)

LC/MS (method LC-A): $R_t$ 1.12 min, $MH^+$ 513

$[\alpha]_D^{20}$: −87.2° (c 0.625, DMF)

Chiral SFC (method SFC-H): $R_t$ 1.85 min, $MH^+$ 513, chiral purity 100%.

Example 4: Synthesis of 1-(6-chloro-1H-indol-3-yl)-2-(4-fluoro-2-methoxyphenyl)-2-((3-(2-hydroxyethoxy)-5-methoxyphenyl)amino)ethanone (Compound 4) and Chiral Separation into Enantiomers 4A and 4B

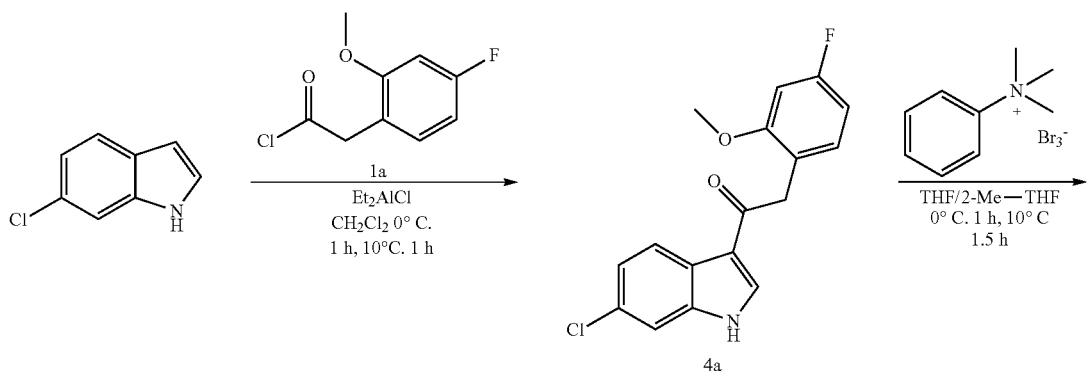

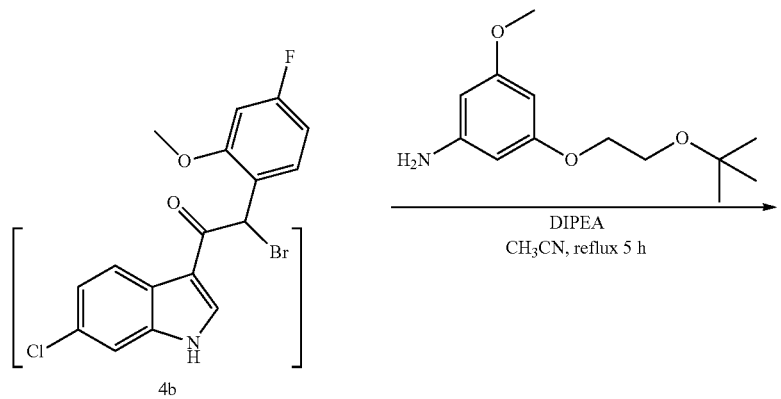

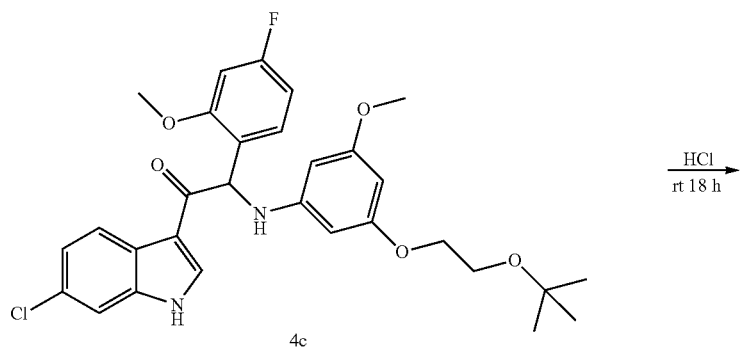

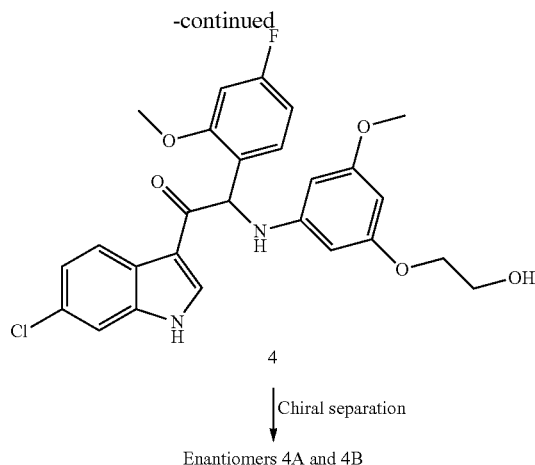

Synthesis of Intermediate 4a:

A stirred solution of 6-chloro-1H-indole [CAS 17422-33-2] (2.23 g, 14.7 mmol) in CH$_2$Cl$_2$ (125 mL) under N$_2$-flow, was cooled to 0° C. using an ice-bath. A solution of diethylaluminum chloride 1M in hexane (22.1 mL, 22.1 mmol) was added dropwise and the mixture was stirred for 10 min at 0° C. Then, a solution of 2-(4-fluoro-2-methoxyphenyl)acetyl chloride 1a (4.47 g, 22.1 mmol, synthesis: see Example 1) in CH$_2$Cl$_2$ (30 mL) was added dropwise over a period of 50 min and the resulting mixture was kept at 0° C. for 1 h and subsequently stirred at 10° C. for 1 h. After cooling to 0° C. again, the reaction was quenched by the slow addition of a solution of potassium sodium tartrate tetrahydrate (Rochelle salt) [CAS 6100-16-9] (8.31 g, 29.4 mmol) in water (9 mL) and the mixture was allowed to warm to room temperature over 1 h. The reaction mixture was diluted by the addition of 2-methyl-THF (150 mL) and stirred for 30 min at room temperature. Na$_2$SO$_4$ (30 g) was added and after stirring for 30 min, the mixture was filtered over Dicalite®. The filter cake was washed several times with 2-methyl-THF and the combined filtrates were concentrated in vacuum to a residual volume of 25 mL. After standing for 2 h, a precipitate was filtered off and dried under vacuum to provide 1-(6-chloro-1H-indol-3-yl)-2-(4-fluoro-2-methoxyphenyl)ethanone 4a (2.85 g).

Synthesis of Intermediate 4c:

A solution of 1-(6-chloro-1H-indol-3-yl)-2-(4-fluoro-2-methoxyphenyl)ethanone 4a (1 g, 3.15 mmol) in 2-methyl-THF (50 mL) was stirred under N$_2$-flow and cooled on an ice-bath. A solution of phenyltrimethylammonium tribromide [CAS 4207-56-1] (1.24 g, 3.31 mmol) in THF (10 mL) and 2-methyl-THF (10 mL) was added dropwise and the mixture was stirred at 0° C. for 1 h and subsequently at 10° C. for 90 min. Then, a solution of 3-(2-(tert-butoxy)ethoxy)-5-methoxyaniline [CAS 1428973-39-0] (0.83 g, 3.46 mmol) and diisopropylethylamine (1.63 mL, 9.44 mmol) in CH$_3$CN (40 mL) was added dropwise and the reaction mixture was heated under reflux for 90 min. The solvents were evaporated under reduced pressure. The residue was taken up in CH$_3$CN (30 mL) and heated under reflux for 5 h. After cooling to room temperature, the solvent was evaporated under vacuum and the residue was purified by flash chromatography on silica (Stationary phase: Grace Reveleris® Silica 80 g, Mobile phase: heptane/EtOAc gradient 100/0 to 0/100). The desired fractions were combined and evaporated, and co-evaporated with 1,4-dioxane to provide 2-((3-(2-(tert-butoxy)ethoxy)-5-methoxyphenyl)amino)-1-(6-chloro-1H-indol-3-yl)-2-(4-fluoro-2-methoxyphenyl)ethanone 4c (1.5 g, LC purity=71%). The crude product was used as such in the next step.

Synthesis of Compound 4 and Chiral Separation of Enantiomers 4A and 4B:

2-((3-(2-(tert-Butoxy)ethoxy)-5-methoxyphenyl)amino)-1-(6-chloro-1H-indol-3-yl)-2-(4-fluoro-2-methoxyphenyl)ethanone 4c (1.5 g, 1.92 mmol) was mixed with hydrochloric acid 4M in dioxane (25 mL, 0.1 mol) and the mixture was stirred at room temperature for 18 h. The mixture was degassed and poured out slowly in an aqueous saturated solution of NaHCO$_3$. The product was extracted twice with 2-methyl-THF and the combined extracts were dried over MgSO$_4$, filtered and evaporated. The residue was purified by flash chromatography on silica (Stationary phase: Biotage® SnapUltra Silica 50 g, Mobile phase: heptane/EtOAc/EtOH gradient 100/0/0 to 60/30/10). The desired fractions were combined and evaporated and subsequently purified via Preparative HPLC (Stationary phase: Uptisphere® C18 ODB-10 µm, 200 g, 5 cm, Mobile phase: 0.25% NH$_4$HCO$_3$ solution in water, CH$_3$CN). The product fractions were combined and evaporated. The residue was co-evaporated from a mixture of MeOH/CH$_3$CN to provide racemic 1-(6-chloro-1H-indol-3-yl)-2-(4-fluoro-2-methoxyphenyl)-2-((3-(2-hydroxyethoxy)-5-methoxyphenyl)amino)-ethanone (Compound 4, 500 mg) as an oil.

Chiral separation of Compound 4 (500 mg) was done via Normal Phase Chiral separation (Stationary phase: AS 20 µm, Mobile phase: 100% MeOH). The product fractions were combined and evaporated. The first eluted product was further purified by flash chromatography on silica (stationary phase: Biotage® SnapUltra Grace Reveleris® Silica 12 g, Mobile phase: heptane/EtOAc gradient 100/0 to 0/100). The product fractions were combined, evaporated under reduced pressure and subsequently co-evaporated with CH$_3$CN. The residue was solidified by lyophilization from CH$_3$CN/water to provide Enantiomer 4A (135 mg) as an amorphous powder. The second eluted product was further purified by flash chromatography on silica (stationary phase: Biotage® SnapUltra GraceReveleris® Silica 12 g, Mobile phase: heptane/EtOAc gradient 100/0 to 0/100). The product fractions were combined and evaporated under reduced pressure. The residue was solidified by lyophilization from CH$_3$CN/water to provide Enantiomer 4B (160 mg) as an amorphous powder.

Compound 4:

LC/MS (method LC-B): $R_t$ 1.99 min, MH+ 499

Enantiomer 4A:

$^1$H NMR (400 MHz, DMSO-$d_6$) δ ppm 3.61 (s, 3H) 3.62-3.66 (m, 2H) 3.77-3.89 (m, 2H) 3.95 (s, 3H) 4.76 (t, J=5.72 Hz, 1H) 5.71 (t, J=2.12 Hz, 1H) 5.93 (d, J=2.14 Hz, 2H) 6.14 (d, J=7.97 Hz, 1H) 6.35 (d, J=8.00 Hz, 1H) 6.72 (td, J=8.49, 2.51 Hz, 1H) 6.92 (dd, J=11.36, 2.52 Hz, 1H) 7.20 (dd, J=8.53, 1.93 Hz, 1H) 7.37 (dd, J=8.60, 6.88 Hz, 1H) 7.52 (d, J=1.92 Hz, 1H) 8.13 (d, J=8.51 Hz, 1H) 8.44 (s, 1H) 12.09 (br. s, 1H)

LC/MS (method LC-A): $R_t$ 1.09 min, MH+ 499

$[α]_D^{20}$: +107.4° (c 0.565, DMF)

Chiral SFC (method SFC-I): $R_t$ 1.54 min, MH+ 499, chiral purity 100%.

Enantiomer 4B:

$^1$H NMR (360 MHz, DMSO-$d_6$) δ ppm 3.61 (s, 3H) 3.64 (t, J=4.93 Hz, 2H) 3.76-3.90 (m, 2H) 3.95 (s, 3H) 4.80 (br. s., 1H) 5.71 (t, J=2.09 Hz, 1H) 5.93 (d, J=2.12 Hz, 2H) 6.14 (d, J=8.03 Hz, 1H) 6.39 (d, J=8.05 Hz, 1H) 6.73 (td, J=8.48, 2.46 Hz, 1H) 6.93 (dd, J=11.37, 2.48 Hz, 1H) 7.21 (dd, J=8.52, 1.94 Hz, 1H) 7.37 (dd, J=8.59, 6.88 Hz, 1H) 7.53 (d, J=1.93 Hz, 1H) 8.14 (d, J=8.53 Hz, 1H) 8.46 (s, 1H) 12.12 (br. s, 1H)

LC/MS (method LC-A): $R_t$ 1.08 min, MH+ 499

$[α]_D^{20}$: −102.6° (c 0.5295, DMF)

Chiral SFC (method SFC-I): $R_t$ 1.90 min, MH+ 499, chiral purity 100%.

Example 5: Synthesis of 1-(6,7-difluoro-1H-indol-3-yl)-2-(4-fluoro-2-methoxy-phenyl)-2-((3-(2-hydroxyethoxy)-5-methoxyphenyl)amino)ethanone (Compound 5) and Chiral Separation into Enantiomers 5A and 5B

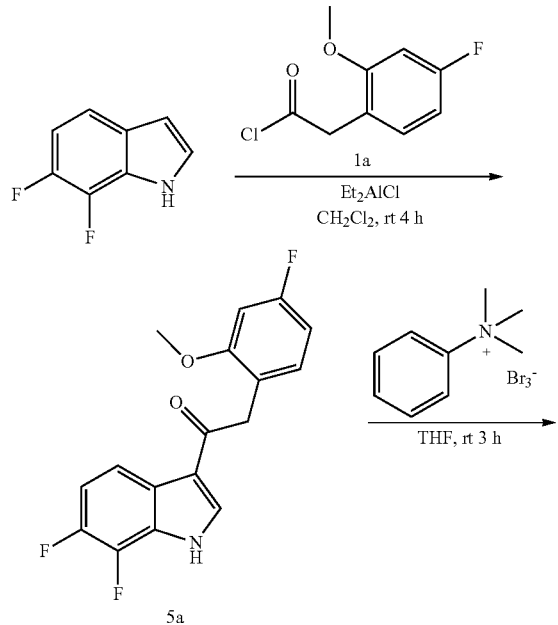

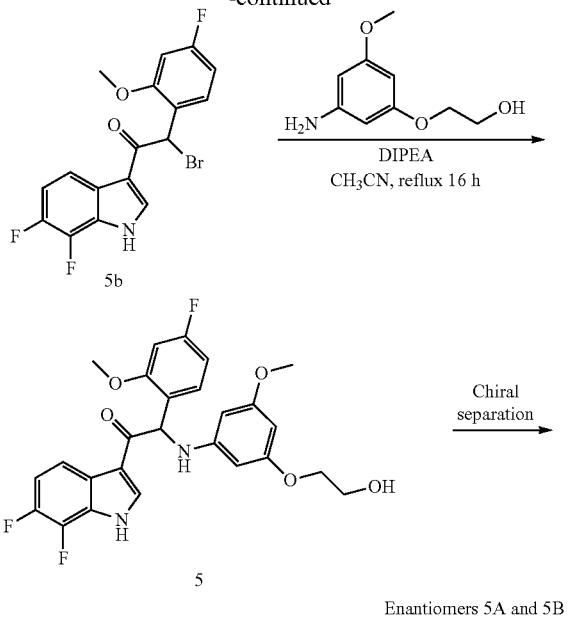

Enantiomers 5A and 5B

Synthesis of Intermediate 5a:

A solution of 6,7-difluoro-1H-indole [CAS 271780-84-8] (3.0 g, 19.6 mmol) in $CH_2Cl_2$ (75 mL) was stirred under $N_2$ and cooled on ice. A solution of diethylaluminum chloride 1M in hexane (30 mL, 30 mmol) was added dropwise and the mixture was stirred for 10 min at 0° C. Then, a solution of 2-(4-fluoro-2-methoxyphenyl)acetyl chloride 1a (5.0 g, 24.7 mmol, synthesis: see Example 1) in $CH_2Cl_2$ (15 mL) was added dropwise and the resulting mixture was stirred at room temperature for 4 h. The reaction mixture was poured out slowly into a cooled (0° C.) aqueous saturated solution of $NaHCO_3$. The mixture was filtered over Dicalite® and the filter cake was washed with THF. From the combined filtrates, the organic layer was separated, dried over $MgSO_4$, filtered and evaporated under reduced pressure. The solid residue was triturated with $CH_2Cl_2$, the solids were filtered off and dried in vacuum at 50° C. to give 1-(6,7-difluoro-1H-indol-3-yl)-2-(4-fluoro-2-methoxyphenyl)ethanone 5a (4.46 g) as a white powder.

Synthesis of Intermediate 5b:

1-(6,7-Difluoro-1H-indol-3-yl)-2-(4-fluoro-2-methoxyphenyl)ethanone 5a (4.45 g, 13.93 mmol) was suspended in THF (60 mL) and cooled on ice under $N_2$. A solution of phenyltrimethylammonium tribromide [CAS 4207-56-1] (5.30 g, 14.1 mmol) in THF (35 mL) was added dropwise and the mixture was subsequently stirred at room temperature for 3 h. The precipitate was filtered off and washed with THF. The combined filtrates were evaporated under reduced pressure. The residue was triturated with a small amount of $CH_2Cl_2$, filtered off and dried under vacuum at 50° C. to provide 2-bromo-1-(6,7-difluoro-1H-indol-3-yl)-2-(4-fluoro-2-methoxyphenyl)ethanone 5b (4.10 g) as a white powder.

Synthesis of Compound 5 and Chiral Separation into Enantiomers 5A and 5B:

A mixture 2-bromo-1-(6,7-difluoro-1H-indol-3-yl)-2-(4-fluoro-2-methoxyphenyl)-ethanone 5b (4.10 g, 10.31 mmol), 2-(3-amino-5-methoxyphenoxy)ethanol [CAS 725237-16-1] (1.91 g, 10.43 mmol), and diisopropylethylamine (1.8 mL, 10.44 mmol) was stirred in $CH_3CN$ and heated under reflux overnight. After cooling to room temperature, the solvents were evaporated under reduced pressure and the residue was purified by flash chromatography on silica (Stationary phase: Silica 340 g HP-Spher 25 μm, Mobile phase: CH$_2$Cl$_2$/EtOAc gradient 100/0 to 50/50). The product fractions were combined and evaporated under reduced pressure. The residue was further purified via Preparative HPLC (Stationary phase: Uptisphere® C18 ODB-10 μm, 200 g, 5 cm. Mobile phase: 0.25% NH$_4$HCO$_3$ solution in water, MeOH). The product fractions were concentrated, dissolved in methanol and concentrated again yielding 1-(6,7-difluoro-1H-indol-3-yl)-2-(4-fluoro-2-methoxyphenyl)-2-((3-(2-hydroxyethoxy)-5-methoxyphenyl)amino)ethanone (Compound 5, 1.62 g) as a racemic mixture. A small fraction of this batch was solidified by lyophilization from a mixture of CH$_3$CN/water to provide Compound 5 (65 mg) as an amorphous white powder. Chiral separation of Compound 5 (1.50 g) was performed via Preparative SFC (Stationary phase: Chiralcel® Diacel® OD 20×250 mm, Mobile phase: CO$_2$, EtOH with 0.2% iPrNH$_2$). Product fractions were combined and evaporated under reduced pressure. The first eluted product was further purified by column chromatography on silica (Stationary phase: Silica 25 g HP-Spher 25 μm, Mobile phase: CH$_2$Cl$_2$/MeOH gradient 100/0 to 0/100). The product fractions were concentrated to a residual amount of 2 mL. A white precipitate was filtered off, washed several times with CH$_2$Cl$_2$ and dried under vacuum at 50° C. to provide Enantiomer 5A (414 mg) as an amorphous white powder. The second eluted product was further purified by column chromatography on silica (Stationary phase: Silica 25 g HP-Spher 25 μm, Mobile phase: CH$_2$Cl$_2$/MeOH gradient 100/0 to 0/100). The product fractions were concentrated to a residual amount of 2 mL. A white precipitate was filtered off, washed several times with CH$_2$Cl$_2$ and dried under vacuum at 50° C. to provide Enantiomer 5B (437 mg) as an amorphous white powder.

Compound 5:
$^1$H NMR (360 MHz, DMSO-d$_6$) δ ppm 3.61 (s, 3H) 3.64 (q, J=5.36 Hz, 2H) 3.74-3.89 (m, 2H) 3.93 (s, 3H) 4.79 (t, J=5.66 Hz, 1H) 5.71 (t, J=2.01 Hz, 1H) 5.94 (d, J=2.18 Hz, 2H) 6.16 (d, J=8.06 Hz, 1H) 6.38 (d, J=8.06 Hz, 1H) 6.73 (td, J=8.42, 2.55 Hz, 1H) 6.93 (dd, J=11.35, 2.55 Hz, 1H) 7.18-7.27 (m, 1H) 7.37 (dd, J=8.43, 6.95 Hz, 1H) 7.92 (dd, J=8.60, 4.92 Hz, 1H) 8.49 (s, 1H) 12.76 (s, 1H)

LC/MS (method LC-A): R$_t$ 1.07 min, MH$^+$ 501

Enantiomer 5A:
$^1$H NMR (360 MHz, DMSO-d$_6$) δ ppm 3.61 (s, 3H) 3.64 (q, J=5.63 Hz, 2H) 3.75-3.89 (m, 2H) 3.94 (s, 3H) 4.79 (t, J=5.53 Hz, 1H) 5.71 (t, J=2.12 Hz, 1H) 5.95 (d, J=2.22 Hz, 2H) 6.16 (d, J=8.21 Hz, 1H) 6.38 (d, J=8.11 Hz, 1H) 6.73 (td, J=8.52, 2.53 Hz, 1H) 6.93 (dd, J=11.35, 2.62 Hz, 1H) 7.19-7.27 (m, 1H) 7.37 (dd, J=8.55, 6.88 Hz, 1H) 7.92 (dd, J=8.94, 4.36 Hz, 1H) 8.49 (s, 1H) 12.77 (s, 1H)

LC/MS (method LC-A): R$_t$ 1.07 min, MH$^+$ 501
$[\alpha]_D^{20}$: −88.3° (c 0.506, DMF)
Chiral SFC (method SFC-J): R$_t$ 2.46 min, MH$^+$ 501, chiral purity 100%.

Enantiomer 5B:
$^1$H NMR (360 MHz, DMSO-d$_6$) δ ppm 3.61 (s, 3H) 3.64 (q, J=5.05 Hz, 2H) 3.76-3.89 (m, 2H) 3.94 (s, 3H) 4.79 (t, J=5.55 Hz, 1H) 5.71 (t, J=2.16 Hz, 1H) 5.95 (d, J=2.07 Hz, 2H) 6.16 (d, J=8.09 Hz, 1H) 6.38 (d, J=8.15 Hz, 1H) 6.73 (td, J=8.43, 2.69 Hz, 1H) 6.93 (dd, J=11.35, 2.67 Hz, 1H) 7.16-7.28 (m, 1H) 7.37 (dd, J=8.55, 6.87 Hz, 1H) 7.92 (dd, J=8.92, 4.37 Hz, 1H) 8.49 (s, 1H) 12.77 (br. s, 1H)

LC/MS (method LC-A): R$_t$ 1.07 min, MH$^+$ 501
$[\alpha]_D^{20}$: +90.3° (c 0.523, DMF)
Chiral SFC (method SFC-J): R$_t$ 4.27 min, MH$^+$ 501, chiral purity 100%.

Example 6: Synthesis of 2-(4-fluoro-2-methoxyphenyl)-2-((3-(2-hydroxyethoxy)-5-methoxyphenyl)amino)-1-(6-methoxy-5-methyl-1H-indol-3-yl)ethanone (Compound 6) and Chiral Separation into Enantiomers 6A and 6B

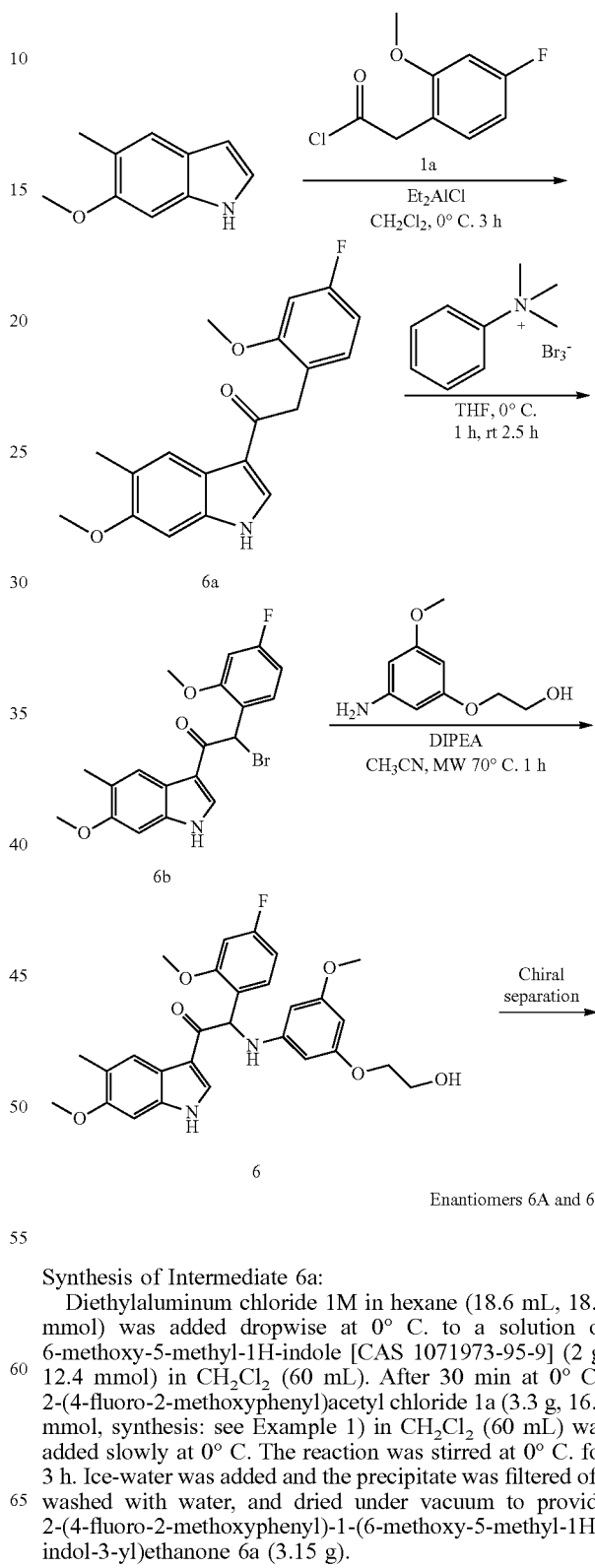

Enantiomers 6A and 6B

Synthesis of Intermediate 6a:
Diethylaluminum chloride 1M in hexane (18.6 mL, 18.6 mmol) was added dropwise at 0° C. to a solution of 6-methoxy-5-methyl-1H-indole [CAS 1071973-95-9] (2 g, 12.4 mmol) in CH$_2$Cl$_2$ (60 mL). After 30 min at 0° C., 2-(4-fluoro-2-methoxyphenyl)acetyl chloride 1a (3.3 g, 16.3 mmol, synthesis: see Example 1) in CH$_2$Cl$_2$ (60 mL) was added slowly at 0° C. The reaction was stirred at 0° C. for 3 h. Ice-water was added and the precipitate was filtered off, washed with water, and dried under vacuum to provide 2-(4-fluoro-2-methoxyphenyl)-1-(6-methoxy-5-methyl-1H-indol-3-yl)ethanone 6a (3.15 g).

Synthesis of Intermediate 6b:

At 0° C., a solution of phenyltrimethylammonium tribromide [CAS 4207-56-1] (3.8 g, 10.1 mmol) in THF (90 mL) was added dropwise to a mixture of 2-(4-fluoro-2-methoxyphenyl)-1-(6-methoxy-5-methyl-1H-indol-3-yl)ethanone 6a (3.15 g, 9.6 mmol) in THF (90 mL). The mixture was stirred at 0° C. for 1 h and at room temperature for 2.5 h. The precipitate was filtered off and washed with EtOAc. The filtrate was concentrated under reduced pressure. The resulting residue was taken up with a minimum amount of $CH_3CN$ and diisopropylether. The precipitate was filtered off and dried under vacuum to provide 2-bromo-2-(4-fluoro-2-methoxyphenyl)-1-(6-methoxy-5-methyl-1H-indol-3-yl)ethanone 6b (2.8 g).

Synthesis of Compound 6 and Chiral Separation into Enantiomers 6A and 6B:

A mixture of 2-bromo-2-(4-fluoro-2-methoxyphenyl)-1-(6-methoxy-5-methyl-1H-indol-3-yl)ethanone 6b (1.0 g, 2.46 mmol), 2-(3-amino-5-methoxyphenoxy)ethanol [CAS 725237-16-1] (676 mg, 3.69 mmol) and diisopropylethylamine (0.64 mL, 3.69 mmol) in $CH_3CN$ (10 mL) and THF (10 mL) was heated at 70° C. for 1 h using a microwave Biotage® Initiator EXP 60 with a power output ranging from 0 to 400 W (fixed hold time). The solvent was evaporated under reduced pressure. The residue was taken up with EtOAc. The organic layer was washed twice with 1N HCl, washed with water, dried over $MgSO_4$, filtered and the solvent was concentrated under reduced pressure. Purification was carried out by flash chromatography on silica gel (15-40 μm, 40 g, $CH_2Cl_2/CH_3OH$ 99.5/0.5). The pure fractions were collected and evaporated to dryness to give 2-(4-fluoro-2-methoxyphenyl)-2-((3-(2-hydroxyethoxy)-5-methoxyphenyl)amino)-1-(6-methoxy-5-methyl-1H-indol-3-yl)ethanone (Compound 6, 330 mg) as a racemic mixture. This fraction was combined with another batch of Compound 6 (60 mg) before chiral separation. Chiral separation of Compound 6 (390 mg) was performed via Preparative Chiral SFC (Stationary phase: Chiralpak® IC 5 μm 250×30 mm, Mobile phase: 70% $CO_2$, 30% MeOH) yielding 137 mg of the first eluted enantiomer and 146 mg of the second eluted enantiomer. The first eluted enantiomer was combined with another batch (fraction 1, total amount: 246 mg). The second eluted enantiomer was combined with another batch (fraction 2, total amount: 245 mg). Fraction 1 was purified again by flash chromatography on silica gel (15-40 μm, 12 g, $CH_2Cl_2/CH_3OH$ 99.5/0.5). The pure fractions were collected and evaporated to dryness to give 207 mg. The compound was solidified from $Et_2O$/heptane and a few drops of $CH_3CN$ to afford Enantiomer 6A (173 mg) as an amorphous powder. Fraction 2 was purified again by flash chromatography on silica gel (15-40 μm, 12 g, $CH_2Cl_2/CH_3OH$ 99.5/0.5). The pure fractions were collected and evaporated to dryness to afford 204 mg. The compound was solidified from $Et_2O$/heptane and a few drops of $CH_3CN$ to afford Enantiomer 6B (158 mg) as an amorphous powder.

Compound 6:

$^1$H NMR (500 MHz, DMSO-$d_6$) δ ppm 2.20 (s, 3H) 3.60 (s, 3H) 3.64 (q, J=5.4 Hz, 2H) 3.77-3.87 (m, 5H) 3.96 (s, 3H) 4.79 (t, J=5.5 Hz, 1H) 5.70 (t, J=2.0 Hz, 1H) 5.92 (d, J=1.6 Hz, 2H) 6.10 (d, J=7.9 Hz, 1H) 6.31 (d, J=7.9 Hz, 1H) 6.72 (td, J=8.5, 2.2 Hz, 1H) 6.89-6.95 (m, 2H) 7.32-7.38 (m, 1H) 7.89 (s, 1H) 8.22 (s, 1H) 11.74 (br. s., 1H)

LC/MS (method LC-C): $R_t$ 2.89 min, MH$^+$ 509

Enantiomer 6A:

$^1$H NMR (500 MHz, DMSO-$d_6$) δ ppm 2.20 (s, 3H) 3.55-3.68 (m, 5H) 3.74-3.91 (m, 5H) 3.96 (s, 3H) 4.78 (t, J=5.5 Hz, 1H) 5.70 (t, J=2.0 Hz, 1H) 5.92 (d, J=2.0 Hz, 2H) 6.10 (d, J=7.9 Hz, 1H) 6.29 (d, J=7.9 Hz, 1H) 6.67-6.76 (m, 1H) 6.88-6.96 (m, 2H) 7.36 (dd, J=8.5, 6.9 Hz, 1H) 7.89 (s, 1H) 8.22 (s, 1H) 11.73 (br. s., 1H)

LC/MS (method LC-C): $R_t$ 2.88 min, MH$^+$ 509

$[\alpha]_D^{20}$: +116.9° (c 0.278, DMF)

Chiral SFC (method SFC-A): $R_t$ 4.07 min, MH$^+$ 509, chiral purity 100%.

Enantiomer 6B:

$^1$H NMR (500 MHz, DMSO-$d_6$) δ ppm 2.20 (s, 3H) 3.55-3.67 (m, 5H) 3.75-3.90 (m, 5H) 3.96 (s, 3H) 4.78 (t, J=5.5 Hz, 1H) 5.70 (t, J=2.0 Hz, 1H) 5.92 (d, J=2.0 Hz, 2H) 6.10 (d, J=7.9 Hz, 1H) 6.29 (d, J=7.9 Hz, 1H) 6.71 (td, J=8.5, 2.4 Hz, 1H) 6.87-6.97 (m, 2H) 7.36 (dd, J=8.5, 6.9 Hz, 1H) 7.89 (s, 1H) 8.22 (s, 1H) 11.73 (br. s., 1H)

LC/MS (method LC-C): $R_t$ 2.88 min, MH$^+$ 509

$[\alpha]_D^{20}$: -118.6° (c 0.279, DMF)

Chiral SFC (method SFC-A): $R_t$ 7.13 min, MH$^+$ 509, chiral purity 100%.

Example 7: Synthesis of 2-(4-fluoro-2-methoxyphenyl)-1-(5-fluoro-6-methoxy-1H-indol-3-yl)-2-((3-(2-hydroxyethoxy)-5-methoxyphenyl)amino)ethanone (Compound 7) and Chiral Separation into Enantiomers 7A and 7B

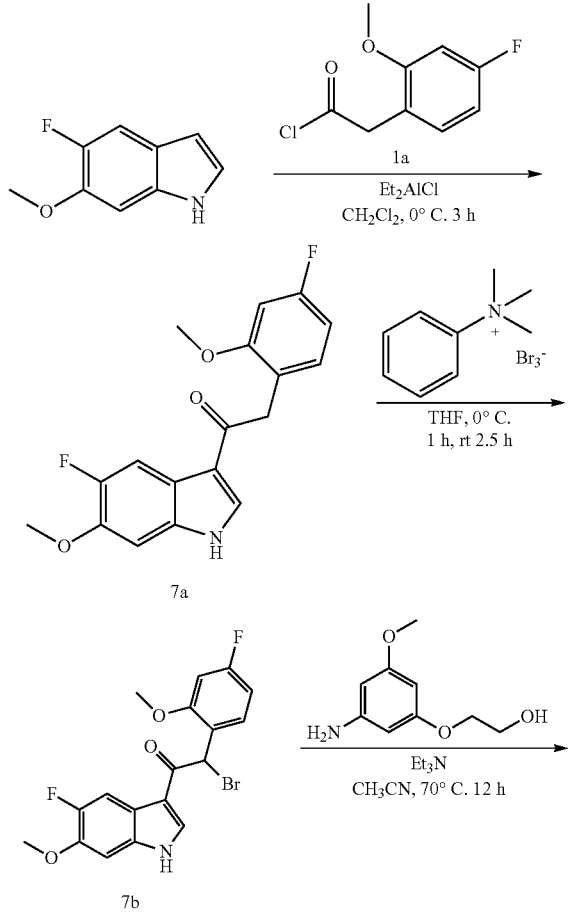

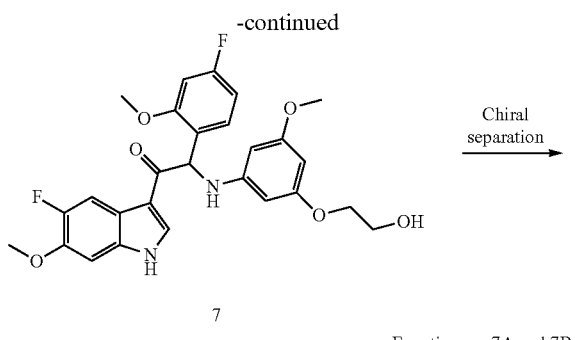

Enantiomers 7A and 7B

Synthesis of Intermediate 7a:

Diethylaluminum chloride 1M in hexane (20 mL, 20 mmol) was added dropwise at 0° C. to a solution of 5-fluoro-6-methoxy-1H-indole [CAS 1211595-72-0] (2.2 g, 13.3 mmol) in $CH_2Cl_2$ (60 mL). After 30 min at 0° C., 2-(4-fluoro-2-methoxyphenyl)acetyl chloride 1a (3.85 g, 19 mmol, synthesis: see Example 1) in $CH_2Cl_2$ (60 mL) was added slowly at 0° C. The reaction was stirred at 0° C. for 3 h. Ice-water and an aqueous solution of $NaHCO_3$ were added. The reaction mixture was extracted with $CH_2Cl_2$/MeOH. The organic layer was washed with water, dried over $MgSO_4$, filtered, and the solvent was concentrated under reduced pressure. The residue was taken up with a minimum of $CH_2Cl_2$. The precipitate was filtered off and dried to afford 2-4-fluoro-2-methoxyphenyl)-1-(5-fluoro-6-methoxy-1H-indol-3-yl)ethanone 7a (3.2 g).

Synthesis of Intermediate 7b:

At 0° C., a solution of phenyltrimethylammonium tribromide [CAS 4207-56-1] (3.22 g, 8.56 mmol) in THF (80 mL) was added dropwise to a mixture of 2-(4-fluoro-2-methoxyphenyl)-1-(5-fluoro-6-methoxy-1H-indol-3-yl)ethanone 7a (2.7 g, 8.15 mmol) in THF (80 mL). The mixture was stirred at 0° C. for 1 h and at room temperature for 2.5 h. The precipitate was filtered-off, washed with EtOAc and water and dried to afford a first batch of 2-bromo-2-(4-fluoro-2-methoxyphenyl)-1-(5-fluoro-6-methoxy-1H-indol-3-yl)ethanone 7b (1.5 g). The organic layer of the filtrate was separated, dried over $MgSO_4$, filtered and concentrated under reduced pressure. The resulting residue was taken up with a minimum amount of $CH_3CN$ and diisopropylether. The precipitate was filtered off and dried under vacuum to give a second batch of 7b (1.7 g).

Synthesis of Compound 7 and Chiral Separation into Enantiomers 7A and 7B:

A mixture of 2-bromo-2-(4-fluoro-2-methoxyphenyl)-1-(5-fluoro-6-methoxy-1H-indol-3-yl)ethanone 7b (0.8 g, 1.95 mmol), 2-(3-amino-5-methoxyphenoxy)ethanol [CAS 725237-16-1] (0.39 g, 2.15 mmol) and triethylamine (0.54 mL, 3.9 mmol) in THF (5 mL) and $CH_3CN$ (5 mL) was stirred at 70° C. for 12 h. The residue was diluted with $CH_2Cl_2$ and $H_2O$. The organic layer was separated, dried over $MgSO_4$, filtered, and the solvent was evaporated under reduced pressure. The crude compound was purified by column chromatography on silica gel (15-40 µm, 40 g in $CH_2Cl_2$/MeOH/$NH_4OH$ (99/1/0.1)). The fractions containing Compound 7 were combined and the solvent was evaporated under reduced pressure. The residue was dissolved in $CH_2Cl_2$ and washed with 1N HCl. The organic layer was separated, dried over $MgSO_4$, filtered and the solvent was concentrated under reduced pressure. A second purification was performed via Reverse Phase HPLC (Stationary phase: X-Bridge®-C18 5 µm 30×150 mm, Mobile phase: gradient from 60% $NH_4HCO_3$ 0.5%/40% MeOH to 0% $NH_4HCO_3$ 0.5%/100% MeOH) to give 2-(4-fluoro-2-methoxyphenyl)-1-(5-fluoro-6-methoxy-1H-indol-3-yl)-2-((3-(2-hydroxyethoxy)-5-methoxyphenyl)amino)ethanone (Compound 7, 350 mg) as a racemic mixture. The Enantiomers were separated via Preparative Chiral SFC (Stationary phase: Chiralpak® IC 5 µm 250×30 mm, Mobile phase: 60% $CO_2$, 40% MeOH) to give 70 mg of Compound 2 as a racemic mixture, 104 mg of the first eluted enantiomer and 100 mg of the second eluted enantiomer. The first eluted enantiomer was crystallized from $CH_3CN/Et_2O$ to afford Enantiomer 7A (76 mg). The second eluted enantiomer was crystallized from $CH_3CN/Et_2O$ to afford Enantiomer 7B (62 mg).

Compound 7:

$^1$H NMR (500 MHz, DMSO-$d_6$) δ ppm 3.56-3.68 (m, 5H) 3.76-3.88 (m, 5H) 3.95 (s, 3H) 4.78 (t, J=5.4 Hz, 1H) 5.70 (s, 1H) 5.92 (s, 2H) 6.11 (d, J=7.9 Hz, 1H) 6.35 (d, J=7.9 Hz, 1H) 6.72 (td, J=8.4, 2.0 Hz, 1H) 6.92 (dd, J=11.0, 1.9 Hz, 1H) 7.14 (d, J=7.6 Hz, 1H) 7.36 (t, J=7.7 Hz, 1H) 7.81 (d, J=12.0 Hz, 1H) 8.33 (s, 1H) 11.93 (br. s., 1H)

LC/MS (method LC-C): $R_t$ 2.74 min, MH$^+$ 513

Enantiomer 7A:

$^1$H NMR (500 MHz, DMSO-$d_6$) δ ppm 3.59-3.67 (m, 5H) 3.77-3.88 (m, 5H) 3.95 (s, 3H) 4.78 (t, J=5.5 Hz, 1H) 5.71 (t, J=1.6 Hz, 1H) 5.92 (d, J=1.6 Hz, 2H) 6.11 (d, J=7.9 Hz, 1H) 6.35 (d, J=7.9 Hz, 1H) 6.72 (td, J=8.4, 2.2 Hz, 1H) 6.92 (dd, J=11.3, 2.2 Hz, 1H) 7.14 (d, J=7.3 Hz, 1H) 7.31-7.41 (m, 1H) 7.81 (d, J=11.7 Hz, 1H) 8.33 (s, 1H) 11.71-12.11 (m, 1H)

LC/MS (method LC-C): $R_t$ 2.74 min, MH$^+$ 513

$[α]_D^{20}$: +85.7° (c 0.28, DMF)

Chiral SFC (method SFC-B): $R_t$ 1.87 min, MH$^+$ 513, chiral purity 100%.

Melting point: 226° C.

Enantiomer 7B:

$^1$H NMR (500 MHz, DMSO-$d_6$) δ ppm 3.58-3.66 (m, 5H) 3.76-3.87 (m, 5H) 3.95 (s, 3H) 4.78 (t, J=5.5 Hz, 1H) 5.70 (t, J=1.6 Hz, 1H) 5.92 (d, J=1.6 Hz, 2H) 6.11 (d, J=7.9 Hz, 1H) 6.35 (d, J=7.9 Hz, 1H) 6.72 (td, J=8.4, 2.2 Hz, 1H) 6.92 (dd, J=11.3, 2.2 Hz, 1H) 7.14 (d, J=7.3 Hz, 1H) 7.36 (t, J=7.7 Hz, 1H) 7.81 (d, J=11.7 Hz, 1H) 8.33 (s, 1H) 11.92 (br. s., 1H)

LC/MS (method LC-C): $R_t$ 2.74 min, MH$^+$ 513

$[α]_D^{20}$: −87.6° (c 0.283, DMF)

Chiral SFC (method SFC-B): $R_t$ 3.24 min, MH$^+$ 513, chiral purity 100%.

Melting point: 226° C.

Example 8: Synthesis of 1-(7-chloro-6-methoxy-1H-indol-3-yl)-2-(4-fluoro-2-methoxyphenyl)-2-((3-(2-hydroxyethoxy)-5-methoxyphenyl)amino)ethanone (Compound 8) and Chiral Separation into Enantiomers 8A and 8B

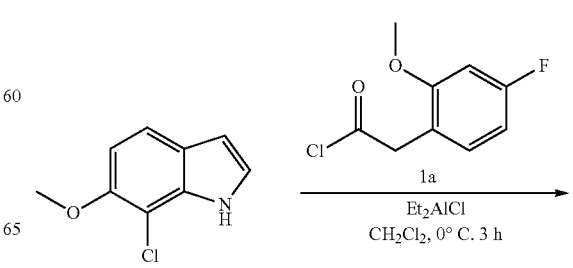

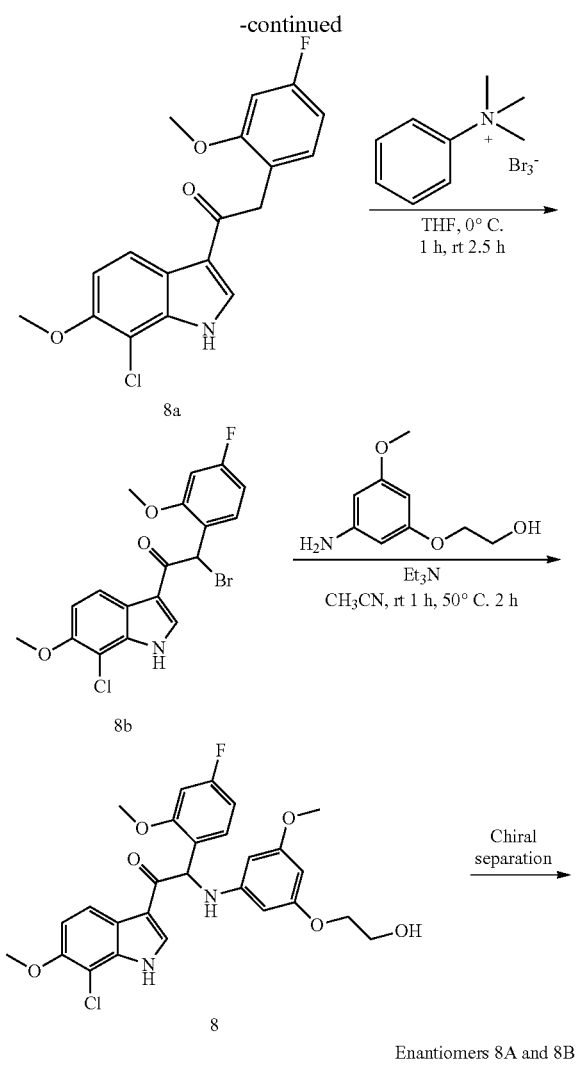

8a

8b

8

Enantiomers 8A and 8B

Synthesis of Intermediate 8a:

Diethylaluminum chloride 1M in hexane (16.5 mL, 16.5 mmol) was added dropwise at 0° C. to a solution of 7-chloro-6-methoxy-1H-indole [CAS 1227604-21-8] (2 g, 11 mmol) in $CH_2Cl_2$ (60 mL). After 30 min at 0° C., 2-(4-fluoro-2-methoxyphenyl)acetyl chloride 1a (3.3 g, 16.3 mmol, synthesis: see Example 1) in $CH_2Cl_2$ (60 mL) was added slowly at 0° C. The reaction was stirred at 0° C. for 3 h. Ice-water was added and the precipitate was filtered off, washed with water, and dried under vacuum to give 1-(7-chloro-6-methoxy-1H-indol-3-yl)-2-(4-fluoro-2-methoxyphenyl)ethanone 8a (2.7 g).

Synthesis of Intermediate 8b:

At 0° C., a solution of phenyltrimethylammonium tribromide [CAS 4207-56-1] (3.06 g, 8.15 mmol) in THF (80 mL) was added dropwise to a mixture of 1-(7-chloro-6-methoxy-1H-indol-3-yl)-2-(4-fluoro-2-methoxyphenyl)ethanone 8a (2.7 g, 7.76 mmol) in THF (80 mL). The mixture was stirred at 0° C. for 1 h and at room temperature for 2.5 h. The precipitate was filtered off, washed with EtOAc. The filtrate was concentrated under reduced pressure, solubilized again in EtOAc and washed with water. The organic layer was separated, dried over $MgSO_4$, filtered and concentrated under reduced pressure. The resulting residue was taken up with a minimum amount of $CH_3CN$ and diisopropylether.

The precipitate was filtered off and dried under vacuum to give 2-bromo-1-(7-chloro-6-methoxy-1H-indol-3-yl)-2-(4-fluoro-2-methoxyphenyl)ethanone 8b (3.2 g).

Synthesis of Compound 8 and Chiral Separation into Enantiomers 8A and 8B:

A mixture of 2-bromo-1-(7-chloro-6-methoxy-1H-indol-3-yl)-2-(4-fluoro-2-methoxyphenyl)ethanone 8b (2 g, 4.69 mmol), 2-(3-amino-5-methoxyphenoxy)ethanol [CAS 725237-16-1] (0.86 g, 4.69 mmol) and triethylamine (1.3 mL, 9.4 mmol) in $CH_3CN$ (100 mL) was stirred at room temperature for 1 h, and then at 50° C. for 2 h. The crude product was purified by column chromatography on silica gel (15-40 μm, 80 g) in toluene/2-propanol/$NH_4OH$ (90/10/0.1)) to provide 800 mg of crude Compound 8. Part of this batch was crystallized from diisopropylether to give a first batch of 1-(7-chloro-6-methoxy-1H-indol-3-yl)-2-(4-fluoro-2-methoxyphenyl)-2-((3-(2-hydroxyethoxy)-5-methoxyphenyl)amino)ethanone (Compound 8, 90 mg). Purification of the remaining material of crude Compound 8 was performed via column chromatography (Stationary phase: irregular bare silica 40 g, Mobile phase: 0.3% $NH_4OH$, 97% $CH_2Cl_2$, 3% MeOH) to give Compound 8 (500 mg) as a racemic mixture.

The enantiomers were separated via Chiral SFC (Stationary phase: Chiralpak® IC 5 μm 250×30 mm, Mobile phase: 55% $CO_2$, 45% MeOH) to give 184 mg of the first eluted enantiomer and 190 mg of the second eluted enantiomer. The first eluted enantiomer was crystallized from heptane/diisopropylether/$CH_3CN$ to afford Enantiomer 8A (135 mg) as an amorphous solid. The second eluted enantiomer was crystallized from heptane/diisopropylether/$CH_3CN$ to afford Enantiomer 8B (150 mg) as an amorphous solid.

Compound 8:

$^1$H NMR (500 MHz, DMSO-$d_6$) δ ppm 3.59-3.67 (m, 5H) 3.77-3.90 (m, 5H) 3.95 (s, 3H) 4.78 (t, J=5.4 Hz, 1H) 5.71 (s, 1H) 5.94 (d, J=1.6 Hz, 2H) 6.14 (d, J=8.2 Hz, 1H) 6.35 (d, J=7.9 Hz, 1H) 6.72 (td, J=8.5, 2.2 Hz, 1H) 6.93 (dd, J=11.3, 2.2 Hz, 1H) 7.10 (d, J=8.8 Hz, 1H) 7.32-7.40 (m, 1H) 8.04 (d, J=8.8 Hz, 1H) 8.33 (s, 1H) 12.16 (br. s., 1H)

LC/MS (method LC-C): $R_t$ 2.89 min, MH$^+$ 529

Enantiomer 8A:

$^1$H NMR (400 MHz, DMSO-$d_6$) δ ppm 3.54-3.68 (m, 5H) 3.73-3.90 (m, 5H) 3.95 (s, 3H) 4.78 (t, J=5.6 Hz, 1H) 5.71 (t, J=2.0 Hz, 1H) 5.94 (d, J=2.0 Hz, 2H) 6.14 (d, J=8.1 Hz, 1H) 6.36 (d, J=8.1 Hz, 1H) 6.72 (td, J=8.5, 2.3 Hz, 1H) 6.93 (dd, J=11.1, 2.3 Hz, 1H) 7.10 (d, J=8.6 Hz, 1H) 7.36 (dd, J=8.6, 7.1 Hz, 1H) 8.04 (d, J=8.6 Hz, 1H) 8.33 (s, 1H) 12.03-12.26 (m, 1H)

LC/MS (method LC-C): $R_t$ 2.88 min, MH$^+$ 529

$[α]_D^{20}$: +84.3° (c 0.267, DMF)

Chiral SFC (method SFC-C): $R_t$ 4.82 min, MH$^+$ 529, chiral purity 100%.

Enantiomer 8B:

$^1$H NMR (400 MHz, DMSO-$d_6$) δ ppm 3.58-3.68 (m, 5H) 3.76-3.90 (m, 5H) 3.95 (s, 3H) 4.78 (t, J=5.6 Hz, 1H) 5.71 (s, 1H) 5.94 (s, 2H) 6.14 (d, J=8.1 Hz, 1H) 6.35 (d, J=8.1 Hz, 1H) 6.72 (td, J=8.5, 2.3 Hz, 1H) 6.93 (dd, J=11.1, 2.3 Hz, 1H) 7.10 (d, J=8.6 Hz, 1H) 7.31-7.41 (m, 1H) 8.04 (d, J=8.6 Hz, 1H) 8.33 (s, 1H) 12.06-12.31 (m, 1H)

LC/MS (method LC-C): $R_t$ 2.88 min, MH$^+$ 529

$[α]_D^{20}$: −84.7° (c 0.268, DMF)

Chiral SFC (method SFC-C): $R_t$ 6.42 min, MH$^+$ 529, chiral purity 99.36%.

Example 9: Synthesis of 2-(4-fluoro-2-methoxyphenyl)-1-(5-fluoro-7-methyl-1H-indol-3-yl)-2-((3-(2-hydroxyethoxy)-5-methoxyphenyl)amino)ethanone (Compound 9) and Chiral Separation into Enantiomers 9A and 9B

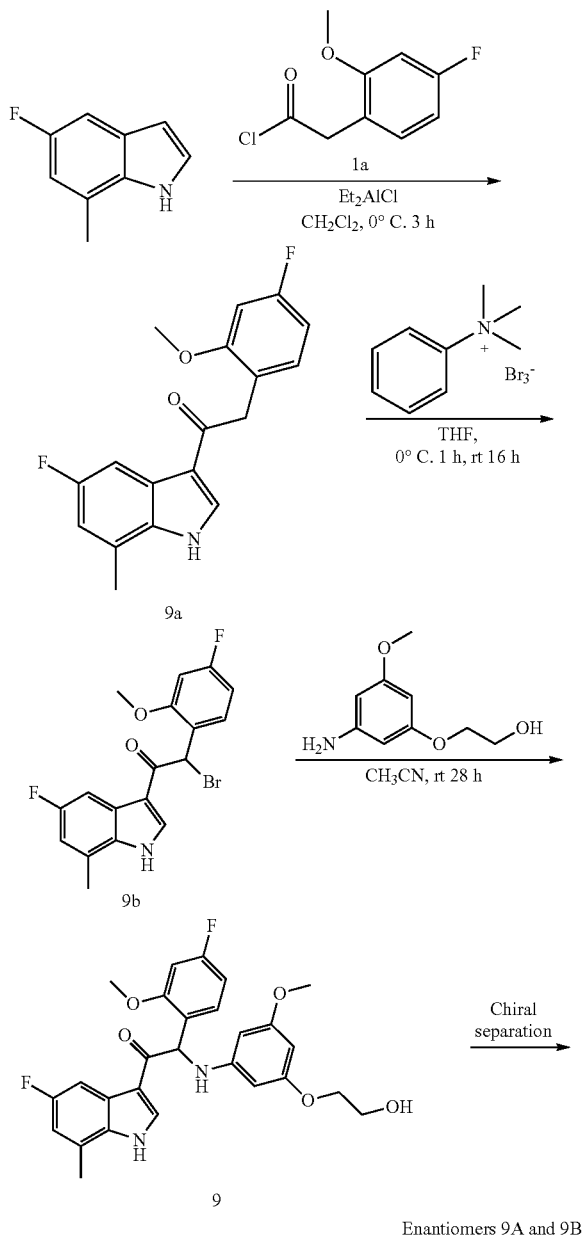

Enantiomers 9A and 9B

Synthesis of Intermediate 9a:

Diethylaluminum chloride 1M in hexane (22 mL, 22 mmol) was added dropwise at 0° C. to a solution of 5-fluoro-7-methyl-1H-indole [CAS 1082041-52-8] (1.62 g, 10.9 mmol) in $CH_2Cl_2$ (45 mL). After 30 min at 0° C., a solution of 2-(4-fluoro-2-methoxyphenyl)acetyl chloride 1a (3.3 g, 16.3 mmol, synthesis: see Example 1) in $CH_2Cl_2$ (30 mL) was added slowly at 0° C. The reaction was stirred at 0° C. for 3 h. Rochelle salt solution (1N, 75 mL) was added and the reaction mixture was stirred at room temperature overnight. The precipitate was filtered off and partitioned between in EtOAc and 1N HCl. The organic phase was washed with 1N HCl and brine, dried over $MgSO_4$, filtered and concentrated under reduced pressure. The residue was taken up with a minimum amount of EtOAc. The precipitate was filtered off to give 2-(4-fluoro-2-methoxyphenyl)-1-(5-fluoro-7-methyl-1H-indol-3-yl)ethanone 9a (2.4 g).

Synthesis of Intermediate 9b:

A solution of phenyltrimethylammonium tribromide [CAS 4207-56-1] (2.2 g, 5.85 mmol) in THF (60 mL) was added dropwise at 0° C. to a solution of 2-(4-fluoro-2-methoxyphenyl)-1-(5-fluoro-7-methyl-1H-indol-3-yl)ethanone 9a (1.66 g, 5.26 mmol) in THF (45 mL). The mixture was stirred at 0° C. for 1 h and at room temperature overnight. The precipitate was filtered off and washed with EtOAc. The filtrate was concentrated under reduced pressure to give 2-bromo-2-(4-fluoro-2-methoxyphenyl)-1-(5-fluoro-7-methyl-1H-indol-3-yl)ethanone 9b (1.9 g).

Synthesis of Compound 9 and Chiral Separation into Enantiomers 9A and 9B:

A mixture of 2-bromo-2-(4-fluoro-2-methoxyphenyl)-1-(5-fluoro-7-methyl-1H-indol-3-yl)ethanone 9b (0.202 g, 0.512 mmol) and 2-(3-amino-5-methoxyphenoxy)ethanol [CAS 725237-16-1] (0.468 g, 2.554 mmol) in $CH_3CN$ (2 mL) and THF (2 mL) was stirred at room temperature for 28 h. The reaction mixture was diluted with EtOAc and washed with 1N HCl. The organic phase was washed with an aqueous saturated $NaHCO_3$ solution and brine, dried over $MgSO_4$, filtered and concentrated under reduced pressure. The residue was purified by flash chromatography on silica gel (10 g) using a gradient of isopropanol (10% to 40%) in heptane. The fractions containing expected compound were combined and concentrated under reduced pressure. The residue was triturated with EtOAc and heptane to afford 2-(4-fluoro-2-methoxyphenyl)-1-(5-fluoro-7-methyl-1H-indol-3-yl)-2-((3-(2-hydroxyethoxy)-5-methoxyphenyl) amino)ethanone (Compound 9, 147 mg) as a racemic mixture. Chiral separation of Compound 9 (430 mg) was performed via chiral SFC (Stationary phase: Chiralcel® OD-H 5 μm 250×20 mm, Mobile phase: 55% $CO_2$, 45% MeOH) to give 198 mg of the first eluted enantiomer and 188 mg of the second eluted enantiomer. The first eluted enantiomer was crystallized from $CH_2Cl_2$/diisopropylether to afford Enantiomer 9A (138 mg). The second eluted enantiomer was crystallized from $CH_2Cl_2$/diisopropylether to afford Enantiomer 9B (151 mg).

Compound 9:

$^1$H NMR (300 MHz, DMSO-$d_6$) δ ppm 2.47 (s, 3H) 3.61 (s, 3H) 3.62-3.67 (m, 2H) 3.77-3.89 (m, 2H) 3.96 (s, 3H) 4.79 (t, J=5.1 Hz, 1H) 5.71 (t, J=2.0 Hz, 1H) 5.94 (d, J=2.0 Hz, 2H) 6.14 (d, J=7.9 Hz, 1H) 6.35 (d, J=7.9 Hz, 1H) 6.69-6.73 (m, 1H) 6.89-6.95 (m, 2H) 7.34-7.39 (m, 1H) 7.63-7.67 (m, 1H) 8.45 (s, 1H) 12.21 (br. s., 1H)

LC/MS (method LC-D): $R_t$ 3.9 min, MH$^+$ 497

Enantiomer 9A:

$^1$H NMR (500 MHz, DMSO-$d_6$) δ ppm 2.47 (s, 3H) 3.52-3.67 (m, 5H) 3.76-3.89 (m, 2H) 3.96 (s, 3H) 4.72-4.83 (m, 1H) 5.71 (br. s., 1H) 5.94 (s, 2H) 6.15 (d, J=7.9 Hz, 1H) 6.36 (d, J=7.9 Hz, 1H) 6.69-6.77 (m, 1H) 6.90-6.97 (m, 2H) 7.36 (t, J=7.9 Hz, 1H) 7.62-7.69 (m, 1H) 8.44 (s, 1H) 12.21 (br. s., 1H)

LC/MS (method LC-C): $R_t$ 2.92 min, MH$^+$ 497

$[\alpha]_D^{20}$: −80.0° (c 0.436, DMF)

Chiral SFC (method SFC-D): $R_t$ 2.14 min, MH$^+$ 497, chiral purity 100%.

Melting point: 181° C.

Enantiomer 9B:

$^1$H NMR (500 MHz, DMSO-$d_6$) δ ppm 2.47 (s, 3H) 3.53-3.68 (m, 5H) 3.74-3.88 (m, 2H) 3.96 (s, 3H) 4.78 (t, J=5.4 Hz, 1H) 5.66-5.73 (m, 1H) 5.94 (s, 2H) 6.15 (d, J=7.9 Hz, 1H) 6.36 (d, J=7.9 Hz, 1H) 6.72 (td, J=8.0, 1.6 Hz, 1H) 6.85-6.98 (m, 2H) 7.36 (t, J=8.0 Hz, 1H) 7.65 (dd, J=9.5, 1.6 Hz, 1H) 8.44 (s, 1H) 12.04-12.43 (m, 1H)

LC/MS (method LC-C): $R_t$ 2.93 min, MH$^+$ 497

$[\alpha]_D^{20}$: +81.1° (c 0.388, DMF)

Chiral SFC (method SFC-D): $R_t$ 3.45 min, MH$^+$ 497, chiral purity 100%.

Melting point: 179° C.

Example 10: Synthesis of 1-(5,6-difluoro-1H-indol-3-yl)-2-(4-fluoro-2-methoxy-phenyl)-2-((3-(2-hydroxyethoxy)-5-methoxyphenyl)amino)ethanone (Compound 10) and Chiral Separation into Enantiomers 10A and 10B

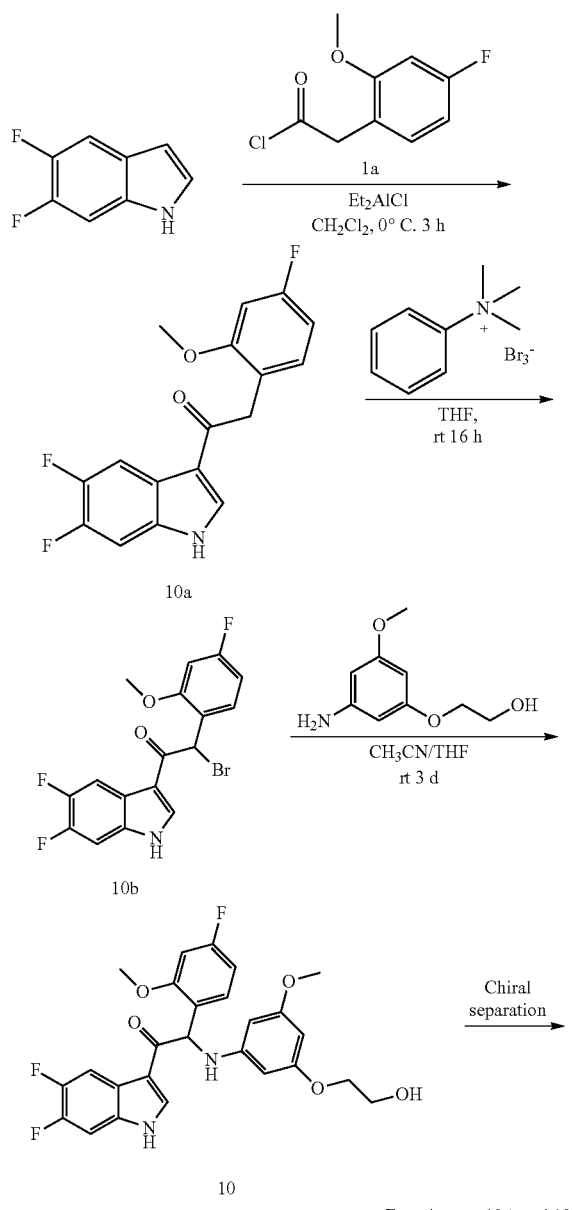

Enantiomers 10A and 10B

Synthesis of Intermediate 10a:

Diethylaluminum chloride 1M in hexane (9.8 mL, 9.8 mmol) was added dropwise at 0° C. to a solution of 5,6-difluoro-1H-indole [CAS 169674-01-5] (1.00 g, 6.5 mmol) in CH$_2$Cl$_2$ (12 mL). After 30 min at 0° C., a solution of 2-(4-fluoro-2-methoxyphenyl)acetyl chloride 1a (1.99 g, 9.8 mmol, synthesis: see Example 1) in CH$_2$Cl$_2$ (3 mL) was added slowly at 0° C. The reaction was stirred at 0° C. for 3 h. 1M Rochelle salt solution was added and the reaction mixture was stirred at room temperature for 30 min. The solids formed were filtered off and partitioned between EtOAc and 1N HCl. The phases were separated. The organic layer was washed with brine, dried over MgSO$_4$, filtered and concentrated under reduced pressure to give 1-(5,6-difluoro-1H-indol-3-yl)-2-(4-fluoro-2-methoxyphenyl)ethanone 10a (1.26 g).

Synthesis of Intermediate 10b:

A solution of phenyltrimethylammonium tribromide [CAS 4207-56-1] (1.63 g, 4.34 mmol) in THF (5 mL) was added dropwise at 0° C. to a solution of 1-(5,6-difluoro-1H-indol-3-yl)-2-(4-fluoro-2-methoxyphenyl)ethanone 10a (1.26 g, 3.95 mmol) in THF (35 mL). The mixture was stirred at room temperature overnight. The precipitate was filtered off and washed with EtOAc. The filtrate was concentrated under reduced pressure. The residue was taken up with a minimum of acetonitrile. The precipitate was filtered off, washed with acetonitrile and dried under vacuum to give 2-bromo-1-(5,6-difluoro-1H-indol-3-yl)-2-(4-fluoro-2-methoxyphenyl)ethanone 10b (0.758 g).

Synthesis of Compound 10 and Chiral Separation into Enantiomers 10A and 10B:

A mixture of 2-bromo-1-(5,6-difluoro-1H-indol-3-yl)-2-(4-fluoro-2-methoxyphenyl)ethanone 10b (0.758 g, 1.90 mmol) and 2-(3-amino-5-methoxyphenoxy)ethanol [CAS 725237-16-1] (0.746 g, 4.07 mmol) in THF (10 mL) and CH$_3$CN (10 mL) was stirred at room temperature for 3 days. The reaction mixture was concentrated under reduced pressure. The residue was partitioned between EtOAc and 1N HCl. The phases were separated. The aqueous phase was extracted with EtOAc. The organic phases were combined, washed with an aqueous saturated NaHCO$_3$ solution and brine, dried over MgSO$_4$, filtered and concentrated under reduced pressure. The residue was purified by flash chromatography on silica gel using a gradient of EtOAc (15% to 100%) in heptane. The fractions containing Compound 10 were combined and concentrated under reduced pressure. A second purification was performed via Reverse Phase HPLC (Stationary phase: X-Bridge®-C18 5 µm 19×100 mm, Mobile phase: gradient from 80% formic acid 0.1%/20% CH$_3$CN to 10% formic acid 0.1%/90% CH$_3$CN) to give 1-(5,6-difluoro-1H-indol-3-yl)-2-(4-fluoro-2-methoxyphenyl)-2-((3-(2-hydroxyethoxy)-5-methoxy-phenyl)amino)ethanone (Compound 10, 499 mg) as a racemic mixture.

The enantiomers of Compound 10 (459 mg) were separated via Preparative Chiral SFC (Stationary phase: Chiralcel® OD-H 5 µm 250×30 mm, Mobile phase: 60% CO$_2$, 40% MeOH) to give 208 mg of the first eluted enantiomer and 221 mg of the second eluted enantiomer. The first eluted enantiomer was solidified from heptane to afford Enantiomer 10A (168 mg). The second eluted enantiomer was solidified from heptane to afford Enantiomer 10B (174 mg).

Compound 10:

$^1$H NMR (300 MHz, DMSO-d$_6$) δ ppm 3.55-3.70 (m, 5H) 3.83 (m, 2H) 3.94 (s, 3H) 4.79 (t, J=5.5 Hz, 1H) 5.72 (s, 1H) 5.93 (d, J=1.9 Hz, 2H) 6.13 (d, J=7.9 Hz, 1H) 6.38 (d, J=8.3 Hz, 1H) 6.73 (td, J=8.5, 2.3 Hz, 1H) 6.93 (dd, J=11.3, 2.3

Hz, 1H) 7.37 (dd, J=8.5, 7.0 Hz, 1H) 7.54 (dd, J=10.7, 7.0 Hz, 1H) 8.00 (dd, J=10.9, 8.3 Hz, 1H) 8.47 (s, 1H) 12.17 (s, 1H)

LC/MS (method LC-E): $R_t$ 8.3 min, MH+ 501

Enantiomer 10A:

$^1$H NMR (500 MHz, DMSO-$d_6$) δ ppm 12.17 (br. s., 1H) 8.47 (s, 1H) 7.99 (dd, J=11.0, 8.2 Hz, 1H) 7.53 (dd, J=10.6, 7.1 Hz, 1H) 7.36 (t, J=7.7 Hz, 1H) 6.92 (dd, J=11.3, 2.2 Hz, 1H) 6.73 (td, J=8.5, 2.2 Hz, 1H) 6.38 (d, J=7.9 Hz, 1H) 6.13 (d, J=7.9 Hz, 1H) 5.93 (s, 2H) 5.71 (br. s, 1H) 4.79 (t, J=5.5 Hz, 1H) 3.94 (s, 3H) 3.82 (m, 2H) 3.57-3.67 (m, 5H)

LC/MS (method LC-C): $R_t$ 2.89 min, MH+ 501

$[\alpha]_D^{20}$: −86.4° (c 0.5727, DMF)

Chiral SFC (method SFC-E): $R_t$ 2.97 min, MH+ 501, chiral purity 100%.

Enantiomer 10B:

$^1$H NMR (500 MHz, DMSO-$d_6$) δ ppm 12.17 (br. s., 1H) 8.47 (s, 1H) 7.99 (dd, J=10.9, 8.4 Hz, 1H) 7.53 (dd, J=10.6, 7.1 Hz, 1H) 7.36 (t, J=7.7 Hz, 1H) 6.92 (dd, J=11.3, 1.6 Hz, 1H) 6.73 (t, J=7.7 Hz, 1H) 6.38 (d, J=8.2 Hz, 1H) 6.13 (d, J=7.9 Hz, 1H) 5.93 (s, 2H) 5.71 (br. s, 1H) 4.79 (t, J=5.5 Hz, 1H) 3.94 (s, 3H) 3.77-3.88 (m, 2H) 3.58-3.67 (m, 5H)

LC/MS (method LC-C): $R_t$ 2.89 min, MH+ 501

$[\alpha]_D^{20}$: +90.7° (c 0.5227, DMF)

Chiral SFC (method SFC-E): $R_t$ 4.67 min, MH+ 501, chiral purity 100%.

Example 11: Synthesis of 2-(4-fluoro-2-methoxyphenyl)-2-((3-(2-hydroxyethoxy)-5-methoxyphenyl)amino)-1-(6-methoxy-7-methyl-1H-indol-3-yl)ethanone (Compound 11) and Chiral Separation into Enantiomers 11A and 11B

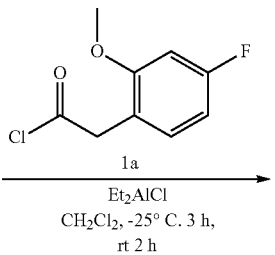

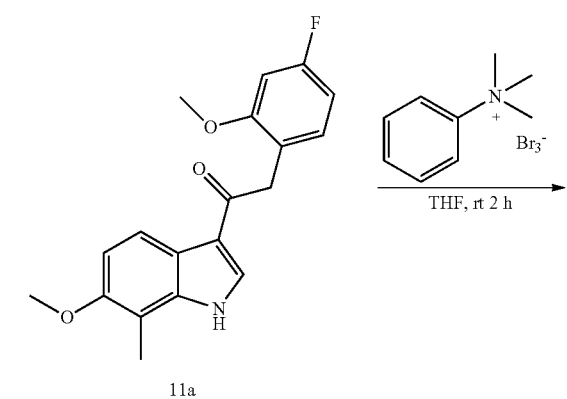

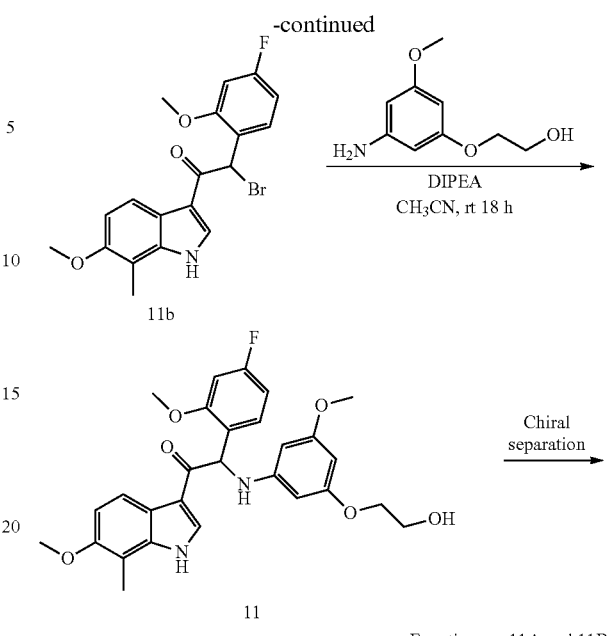

Synthesis of Intermediate 11a:

Diethylaluminum chloride 1M in hexane (40.8 mL, 40.8 mmol) was added dropwise at −25° C. to a solution of 6-methoxy-7-methyl-1H-indole [CAS 19500-05-1] (4.39 g, 27.2 mmol) in $CH_2Cl_2$ (200 mL) under $N_2$-atmosphere. After stirring for 15 min at −25° C., a solution of 2-(4-fluoro-2-methoxyphenyl)acetyl chloride 1a (7.72 g, 38.1 mmol, synthesis: see Example 1) in $CH_2Cl_2$ (200 mL) was added dropwise at −25° C. Stirring was continued at −25° C. for 1 h and the reaction mixture was subsequently allowed to warm to room temperature while stirring for 2 h. The reaction mixture was poured out into an ice-water/Rochelle salt solution, and after stirring for a while, the solids were removed by filtration over Dicalite® and the filter cake was rinsed several times with small portions of THF. The phases were separated and the aqueous layer was extracted with THF. The combined organic layers were washed with brine, dried over $MgSO_4$, filtered and evaporated under reduced pressure. The solid residue was suspended in $CH_2Cl_2$ (20 mL). The solids were filtered off, washed with small portions of $CH_2Cl_2$ and dried under vacuum at 50° C. to give 2-(4-fluoro-2-methoxyphenyl)-1-(6-methoxy-7-methyl-1H-indol-3-yl)ethanone 11a (7.5 g).

Synthesis of Intermediate 11b:

A solution of phenyltrimethylammonium tribromide [CAS 4207-56-1] (5.8 g, 15.5 mmol) in THF (200 mL) was added dropwise at 0° C. to a solution of 2-(4-fluoro-2-methoxyphenyl)-1-(6-methoxy-7-methyl-1H-indol-3-yl)ethanone 11a (4.95 g, 14.1 mmol) in THF (200 mL). The mixture was stirred at room temperature for 2 h. The precipitate was filtered off and washed with THF. The filtrate was concentrated under reduced pressure. The residue was triturated with a small amount of $CH_2Cl_2$. The precipitate was filtered off, washed with $CH_2Cl_2$ and dried under vacuum to give 2-bromo-2-(4-fluoro-2-methoxyphenyl)-1-(6-methoxy-7-methyl-1H-indol-3-yl)ethanone 11b (4.04 g).

Synthesis of Compound 11 and Chiral Separation into Enantiomers 11A and 11B:

A mixture of 2-bromo-2-(4-fluoro-2-methoxyphenyl)-1-(6-methoxy-7-methyl-1H-indol-3-yl)ethanone 11b (1434 mg, 3.78 mmol) and 2-(3-amino-5-methoxy-phenoxy)ethanol [CAS 725237-16-1] (1037 mg, 5.66 mmol) and diisopropylethylamine (976 µL, 5.66 mmol) in CH$_3$CN (100 mL) was stirred at room temperature for 18 h. The reaction mixture was concentrated under reduced pressure. The residue was partitioned between CH$_2$Cl$_2$ and 0.5N HCl. The phases were separated. The organic layer was washed with water, dried over MgSO$_4$, filtered and concentrated under reduced pressure. The residue was purified by flash chromatography on silica gel (Stationary phase: Biotage® SNAP Ultra 100 g, Mobile phase: EtOAc:EtOH (3:1)/heptane gradient 0/100 to 60/40). The fractions containing Compound 11 were combined and concentrated under reduced pressure to give 2-(4-fluoro-2-methoxyphenyl)-2-((3-(2-hydroxyethoxy)-5-methoxyphenyl)amino)-1-(6-methoxy-7-methyl-1H-indol-3-yl)ethanone (Compound 11, 995 mg) as a racemic mixture.

Chiral separation of the enantiomers of Compound 11 (995 mg) was performed using Normal Phase Chiral separation (Stationary phase: (S,S) Whelk-O 1 (500 g), Mobile phase: 100% EtOH, isocratic elution). The product fractions were combined and evaporated to provide Enantiomer 11A as the first eluted product and Enantiomer 11B as the second eluted product. Enantiomers 11A was further purified by column chromatography on silica gel (Stationary phase: Biotage® SNAP Ultra 10 g, Mobile Phase CH$_2$Cl$_2$/MeOH gradient 100/0 to 98/2). The product fractions were combined, the solvent was evaporated under reduced pressure and the residue was dried under vacuum at 50° C. to provide Enantiomer 11A (255 mg) as an amorphous white powder. Enantiomer 11B was further purified by column chromatography on silica gel (Stationary phase: SNAP Ultra 10 g, Mobile Phase CH$_2$Cl$_2$/MeOH gradient 100/0 to 98/2). The product fractions were combined, the solvent was evaporated under reduced pressure and the residue was dried under vacuum at 50° C. to provide Enantiomer 11B (270 mg) as an amorphous white powder.

Compound 11:
$^1$H NMR (400 MHz, DMSO-d$_6$) δ ppm 2.29 (s, 3H) 3.61 (s, 3H) 3.64 (q, J=5.2 Hz, 2H) 3.79 (s, 3H) 3.80-3.90 (m, 2H) 3.97 (s, 3H) 4.77 (t, J=5.4 Hz, 1H) 5.71 (t, J=2.0 Hz, 1H) 5.94 (d, J=2.0 Hz, 2H) 6.13 (d, J=7.9 Hz, 1H) 6.32 (d, J=7.9 Hz, 1H) 6.71 (td, J=8.5, 2.5 Hz, 1H) 6.92 (dd, J=11.3, 2.4 Hz, 1H) 6.94 (d, J=8.8 Hz, 1H) 7.37 (dd, J=8.6, 6.9 Hz, 1H) 7.93 (d, J=8.9 Hz, 1H) 8.31 (d, J=2.9 Hz, 1H) 11.83 (d, J=3.1 Hz, 1H)
LC/MS (method LC-A): R$_t$ 1.10 min, MH$^+$ 509

Enantiomer 11A:
$^1$H NMR (360 MHz, DMSO-d$_6$) δ ppm 2.29 (s, 3H) 3.61 (s, 3H) 3.64 (q, J=5.4 Hz, 2H) 3.79 (s, 3H) 3.80-3.89 (m, 2H) 3.97 (s, 3H) 4.79 (t, J=5.5 Hz, 1H) 5.70 (t, J=2.0 Hz, 1H) 5.94 (d, J=2.2 Hz, 2H) 6.13 (d, J=7.7 Hz, 1H) 6.34 (d, J=7.7 Hz, 1H) 6.72 (td, J=8.4, 2.6 Hz, 1H) 6.93 (dd, J=11.5, 2.4 Hz, 1H) 6.94 (d, J=8.8 Hz, 1H) 7.37 (dd, J=8.6, 6.8 Hz, 1H) 7.93 (d, J=8.8 Hz, 1H) 8.32 (br s, 1H) 11.85 (br s, 1H)
LC/MS (method LC-A): R$_t$ 1.05 min, MH$^+$ 509
[α]$_D^{20}$: +98.8° (c 0.5285, DMF)
Chiral SFC (method SFC-F): R$_t$ 2.26 min, MH$^+$ 509, chiral purity 100%.

Enantiomer 11B:
$^1$H NMR (360 MHz, DMSO-d$_6$) δ ppm 2.29 (s, 3H) 3.61 (s, 3H) 3.64 (q, J=5.1 Hz, 2H) 3.79 (s, 3H) 3.80-3.90 (m, 2H) 3.97 (s, 3H) 4.77 (t, J=5.5 Hz, 1H) 5.70 (t, J=2.0 Hz, 1H) 5.94 (d, J=2.2 Hz, 2H) 6.13 (d, J=8.1 Hz, 1H) 6.34 (d, J=8.1 Hz, 1H) 6.72 (td, J=8.4, 2.6 Hz, 1H) 6.93 (dd, J=11.5, 2.4 Hz, 1H) 6.94 (d, J=8.8 Hz, 1H) 7.37 (dd, J=8.8, 7.0 Hz, 1H) 7.93 (d, J=8.4 Hz, 1H) 8.32 (br s, 1H) 11.85 (br s, 1H)
LC/MS (method LC-A): R$_t$ 1.05 min, MH$^+$ 509
[α]$_D^{20}$: −94.1° (c 0.461, DMF)
Chiral SFC (method SFC-F): R$_t$ 2.73 min, MH$^+$ 509, chiral purity 100%.

Example 12: Synthesis of 2-(4-fluoro-2-methoxyphenyl)-1-(7-fluoro-5-methyl-1H-indol-3-yl)-2-((3-(2-hydroxyethoxy)-5-methoxyphenyl)amino)ethanone (Compound 12) and Chiral Separation into Enantiomers 12A and 12B

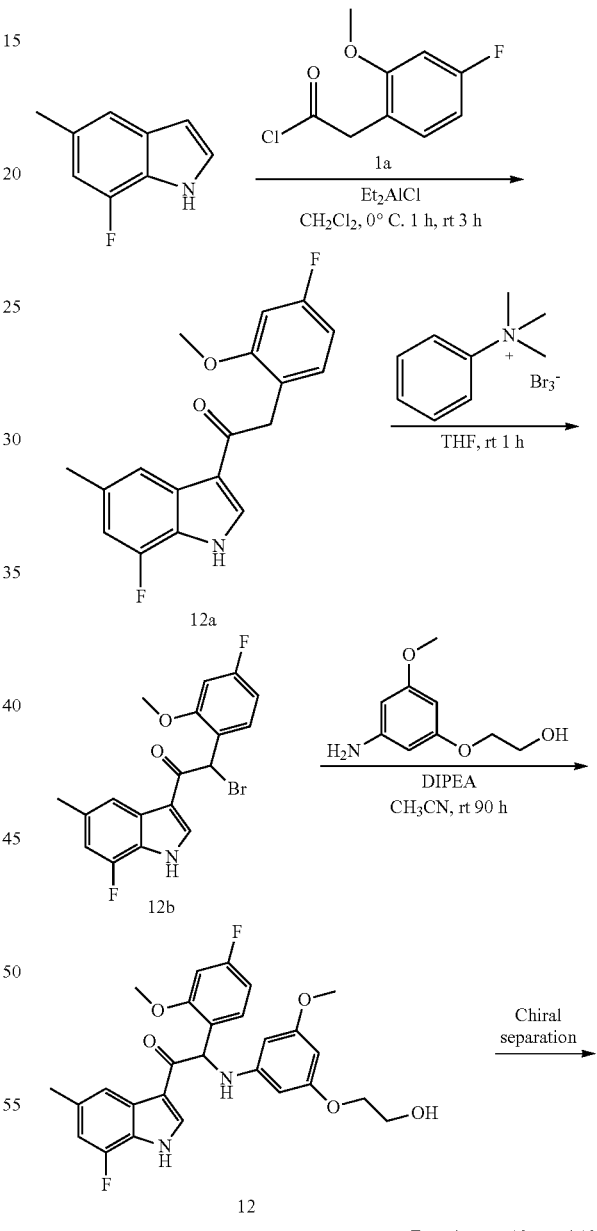

Enantiomers 12A and 12B

Synthesis of Intermediate 12a:
Diethylaluminum chloride 1M in hexane (25.6 mL, 25.6 mmol) was added dropwise at 0° C. to a solution of 7-fluoro-5-methyl-1H-indole [CAS442910-91-0] (2.54 g, 17.0 mmol) in CH$_2$Cl$_2$ (150 mL) under N$_2$-atmosphere.

After stirring for 30 min at 0° C., a solution of 2-(4-fluoro-2-methoxyphenyl)acetyl chloride 1a (5.2 g, 25.6 mmol, synthesis: see Example 1) in $CH_2Cl_2$ (150 mL) was added dropwise at 0° C. Stirring was continued at 0° C. for 1 h and the reaction mixture was subsequently allowed to warm to room temperature while stirring for 3 h. The reaction mixture was poured out into an ice-water/Rochelle salt solution, and after stirring for a while, the solids were removed by filtration over Dicalite® and the filter cake was rinsed several times with small portions of THF. The phases were separated and the aqueous layer was extracted with THF. The combined organic layers were washed with brine, dried over $MgSO_4$, filtered and evaporated under reduced pressure. The solid residue was suspended in $CH_2Cl_2$ (20 mL). The solids were filtered off, washed with small portions of $CH_2Cl_2$/heptane (1/1) and dried under vacuum at 50° C. to give 2-(4-fluoro-2-methoxyphenyl)-1-(7-fluoro-5-methyl-1H-indol-3-yl)ethanone 12a (4.13 g).

Synthesis of Intermediate 12b:

A solution of phenyltrimethylammonium tribromide [CAS 4207-56-1] (5.39 g, 14.3 mmol) in THF (150 mL) was added dropwise at 0° C. to a solution of 2-(4-fluoro-2-methoxyphenyl)-1-(7-fluoro-5-methyl-1H-indol-3-yl)ethanone 12a (4.11 g, 13.0 mmol) in THF (100 mL). The mixture was stirred at room temperature for 1 h. The precipitate was filtered off and washed with THF. The filtrate was concentrated under reduced pressure. The residue was triturated with a small amount of $CH_2Cl_2$. The precipitate was filtered off, washed with $CH_2Cl_2$ and dried under vacuum at 50° C. to give 2-bromo-2-(4-fluoro-2-methoxyphenyl)-1-(7-fluoro-5-methyl-1H-indol-3-yl)ethanone 12b (4.81 g).

Synthesis of Compound 12 and Chiral Separation into Enantiomers 12A and 12B:

A mixture of 2-bromo-2-(4-fluoro-2-methoxyphenyl)-1-(7-fluoro-5-methyl-1H-indol-3-yl)ethanone 12b (1096 mg, 2.78 mmol) and 2-(3-amino-5-methoxyphenoxy)ethanol [CAS 725237-16-1] (764 mg, 4.17 mmol) and diisopropylethylamine (718 μL, 4.17 mmol) in $CH_3CN$ (25 mL) was stirred at room temperature for 90 h. The reaction mixture was concentrated under reduced pressure. The residue was partitioned between $CH_2Cl_2$ and 0.5N HCl. The phases were separated. The organic layer was washed with water, dried over $MgSO_4$, filtered and concentrated under reduced pressure. The residue was purified by flash chromatography on silica gel (Stationary phase: Biotage® SNAP Ultra 100 g, Mobile phase: EtOAc: EtOH(3:1)/heptane gradient 0/100 to 50/50). The fractions containing Compound 12 were combined and concentrated under reduced pressure to give 2-(4-fluoro-2-methoxyphenyl)-1-(7-fluoro-5-methyl-1H-indol-3-yl)-2-((3-(2-hydroxyethoxy)-5-methoxyphenyl)amino)ethanone (Compound 12, 919 mg) as a racemic mixture.

Chiral separation of the enantiomers of Compound 12 (919 mg) was performed via Preparative SFC (Stationary phase: Chiralcel® Diacel® OD 20×250 mm, Mobile phase: $CO_2$, EtOH with 0.2% $iPrNH_2$). The product fractions were combined, evaporated and dried under vacuum at 50° C. to provide Enantiomer 12A (307 mg) as the first eluted product and Enantiomer 12B (302 mg) as the second eluted product. Both enantiomers occurred as amorphous white powders.

Compound 12:
LC/MS (method LC-A): $R_t$ 1.08 min, MH$^+$ 497

Enantiomer 12A:
$^1$H NMR (360 MHz, DMSO-d$_6$) δ ppm 2.39 (s, 3H) 3.62 (s, 3H) 3.65 (q, J=5.4 Hz, 2H) 3.77-3.90 (m, 2H) 3.95 (s, 3H) 4.80 (t, J=5.5 Hz, 1H) 5.72 (t, J=2.0 Hz, 1H) 5.95 (d, J=2.2 Hz, 2H) 6.15 (d, J=8.1 Hz, 1H) 6.35 (d, J=8.1 Hz, 1H) 6.74 (td, J=8.5, 2.4 Hz, 1H) 6.92 (dd, J=12.1, 1.1 Hz, 1H) 6.94 (dd, J=11.3, 2.2 Hz, 1H) 7.37 (dd, J=8.8, 7.0 Hz, 1H) 7.79 (s, 1H) 8.40 (s, 1H) 12.48 (br s, 1H)

LC/MS (method LC-B): $R_t$ 1.98 min, MH$^+$ 497

$[α]_D^{20}$: −113.5° (c 0.355, DMF)

Chiral SFC (method SFC-K): $R_t$ 2.26 min, MH$^+$ 497, chiral purity 100%.

Enantiomer 12B:
$^1$H NMR (360 MHz, DMSO-d$_6$) δ ppm 2.38 (s, 3H) 3.61 (s, 3H) 3.64 (q, J=5.1 Hz, 2H) 3.77-3.89 (m, 2H) 3.94 (s, 3H) 4.79 (t, J=5.5 Hz, 1H) 5.71 (t, J=1.8 Hz, 1H) 5.94 (d, J=1.8 Hz, 2H) 6.15 (d, J=8.1 Hz, 1H) 6.34 (d, J=7.7 Hz, 1H) 6.73 (td, J=8.5, 2.4 Hz, 1H) 6.91 (br d, J=12.1 Hz, 1H) 6.93 (dd, J=11.3, 2.6 Hz, 1H) 7.36 (dd, J=8.4, 7.0 Hz, 1H) 7.78 (s, 1H) 8.39 (s, 1H) 12.46 (br s, 1H)

LC/MS (method LC-B): $R_t$ 1.98 min, MH$^+$ 497

$[α]_D^{20}$: +117.0° (c 0.448, DMF)

Chiral SFC (method SFC-K): $R_t$ 3.67 min, MH$^+$ 497, chiral purity 100%.

Antiviral Activity of the Compounds of the Invention

DENV-2 Antiviral Assay

The antiviral activity of all the compounds of the invention was tested against DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 4-fold serial dilution of 9 dilution steps of the test compound at 200 times the final concentration in 100% DMSO (200 nL). In addition, each compound concentration is tested in quadruplicate (final concentration range: 25 μM-0.00038 μM). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T−S_{CC})/(S_{VC}−S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 10 µL of resazurin, a cell viability stain, was added to all wells of the 384-well plates. The resazurin assay is based on the reduction of the blue resazurin by NADH, produced by the cells, into the highly fluorescent product, resorufin. The formation of pink fluorescent resorufin is directly related to the number of viable cells in the well. The plates were incubated for an additional 5 hours in a fully humidified incubator (37° C., 5% $CO_2$). Next, the plates were measured on an Infinite reader (Tecan) using an excitation wavelength of 530 nm. The half maximal cytotoxic concentration ($CC_{50}$) was also determined, defined as the concentration required to reduce the resazurin conversion by 50% compared to that of the cell control wells (Table 1). Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | EC50 (µM) | N | CC50 (µM) | N | SI | N |
|---|---|---|---|---|---|---|
| 1 | 0.0080 | 4 | 11 | 4 | >1564 | 4 |
| 1A | 0.0038 | 5 | 8.4 | 4 | 2100 | 4 |
| 1B | 0.66 | 5 | 12 | 5 | 18 | 5 |
| 2 | 0.0054 | 4 | 7.0 | 4 | 1291 | 4 |
| 2A | 0.66 | 5 | 5.4 | 4 | 8.1 | 4 |
| 2B | 0.0022 | 5 | 5.3 | 4 | 2581 | 4 |
| 3 | 0.0021 | 3 | 6.3 | 4 | 2915 | 3 |
| 3A | 0.00077 | 6 | 4.1 | 5 | 5120 | 5 |
| 3B | 0.18 | 5 | 5.8 | 5 | 32 | 5 |
| 4A | 0.0016 | 4 | 5.9 | 4 | 3698 | 4 |
| 4B | 0.38 | 4 | 7.7 | 4 | 20 | 4 |
| 5 | 0.0089 | 4 | 5.2 | 4 | 586 | 4 |
| 5A | 0.44 | 5 | 7.4 | 4 | 17 | 4 |
| 5B | 0.0025 | 30 | 6.5 | 30 | 2673 | 29 |
| 6A | 0.0027 | 9 | 7.5 | 8 | 2968 | 8 |
| 6B | 0.29 | 5 | 9.6 | 5 | 33 | 5 |
| 7 | 0.014 | 4 | >9.7 | 4 | 1049 | 4 |
| 7A | 0.0046 | 6 | >8.6 | 5 | 1864 | 5 |
| 7B | 0.54 | 5 | 14 | 5 | 39 | 5 |
| 8 | 0.0039 | 4 | 6.8 | 4 | 1733 | 4 |
| 8A | 0.0010 | 7 | 8.6 | 6 | 10020 | 6 |
| 8B | 0.15 | 5 | 9.1 | 6 | 59 | 5 |
| 9 | 0.0094 | 4 | 7.5 | 4 | 794 | 4 |
| 9A | 0.63 | 6 | 8.8 | 5 | 14 | 5 |
| 9B | 0.0034 | 6 | 5.5 | 5 | 1575 | 5 |
| 10 | 0.0068 | 3 | 9.3 | 3 | 1362 | 3 |
| 10A | 0.58 | 3 | 11 | 3 | 19 | 3 |
| 10B | 0.0027 | 3 | 6.9 | 2 | 2565 | 2 |
| 11 | 0.0024 | 3 | 10 | 2 | 4455 | 2 |
| 11A | 0.00081 | 3 | 8.9 | 3 | 10981 | 3 |
| 11B | 0.41 | 3 | 12 | 3 | 28 | 3 |
| 12A | 0.93 | 3 | 9.2 | 3 | 10 | 3 |
| 12B | 0.0051 | 3 | 5.5 | 3 | 1063 | 3 |

N = the number of independent experiments in which the compounds were tested.

Tetravalent Reverse Transcriptase Quantitative-PCR (RT-qPCR) Assay: Protocol A.

The antiviral activity of the compounds of the invention was tested against DENV-1 strain TC974#666 (NCPV), DENV-2 strain 16681, DENV-3 strain H87 (NCPV) and DENV-4 strains H241 (NCPV) and EDEN (SG/06K2270DK1/2005; GenBank accession number QG398256) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; table 2) and a cellular reference gene (β-actin, table 2). Subsequently, a duplex real time PCR was performed on a Lightcycler480 instrument. The generated Cp value is inversely proportional to the amount of RNA expression of these targets. Inhibition of DENV replication by a test compound result in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values were determined based on the Cp values acquired for the housekeeping gene β-actin.

TABLE 2

Primers and probes used for the real-time, quantitative RT-PCR.

| Primer/probe | Target | Sequence[a, b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM-5'-AAGGACTAGAGGTTAGAGG AGACCCCCC-3'-BHQ1 |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | HEX-5'-TTCCGCTGCCCTGAGGCTCT C-3'-BHQ1 |

[a] Reporter dyes (FAM, HEX) and quencher (BHQ1) elements are indicated in bold and italics.
[b] The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 µL/well was added in 96-well plates (10000 cells/well), which already contain the antiviral compounds. Typically, these plates contain a 4-fold serial dilution of 9 dilution steps of the test compound at 200 times the final concentration in 100% DMSO (500 nL; final concentration range: 25 µM-0.00038 µM). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Then, DENV-1 strain TC974#666, DENV-2 strain 16681, DENV-3 strain H87 or DENV-4 strains H241 or EDEN were added. Therefore, 25 µL of virus suspension, where a Cp of −22 was achieved in RTqPCR, was added to all the wells containing test compound and to the wells assigned as virus control. In parallel, 25 µL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 µL). The cell pellets within the 96-well plates were stored at −80° C. for at least 1 day. Next, RNA was extracted using the Cells-to-CT™ lysis kit, according to the manufacture's guideline (Applied Biosystems). The cell lysates can be stored at −80° C. or immediately used in the reverse transcription step. In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), dispensed in 96-well LightCycler qPCR plates to which 3 μL of cDNA was added and the qPCR was performed according to the conditions in table 4B on a LightCycler 480. Using the LightCycler software and an in-house LIMS system, dose response curves for each compound were calculated and the half maximal effective concentration ($EC_{50}$) and the half maximal cytotoxic concentration ($CO_{50}$) were determined (Tables 6-9).

TABLE 3 cDNA synthesis using Mix A, denaturation, Mix B and reverse transcription.

A Mix A

| | | | Reaction Vol. (μl) 20 |
|---|---|---|---|
| Plates 8 | | | |
| Samples 828 | | | Volume for (μl) |
| | Concentration | | x |
| Mix Item | Unit | Stock | Final | 1 sample | samples |

| Mix Item | Unit | Stock | Final | 1 sample | samples |
|---|---|---|---|---|---|
| Milli-Q H$_2$O | | | | 7.27 | 6019.56 |
| R3utr425 | μM | 20 | 0.27 | 0.15 | 124.20 |
| Ractin876 | μM | 20 | 0.27 | 0.15 | 124.20 |
| | | | Volume mix/well (μl) | 7.57 | |
| | | | Cell lysates | 5.00 | |

B Denaturation step:

| Step | Temp | Time |
|---|---|---|
| Denaturation | 75° C. | 5' |
| Hold | 4° C. | hold |

C Mix B

| | | | | | |
|---|---|---|---|---|---|
| Samples 864 | | | | Volume for (μl) | |
| | Concentration | | | | x |
| Mix Item | Unit | Stock | Final | 1 sample | samples |
| Expand HIFI buffer 2 | X | 10.00 | 1.00 | 2.00 | 1728.0 |
| MgCl$_2$ | mM | 25.00 | 3.50 | 2.80 | 2419.2 |
| dNTPs | mM | 10.00 | 1.00 | 2.00 | 1728.0 |
| Rnase inhibitor | U/μl | 40.00 | 1.00 | 0.50 | 432.0 |
| Expand RT | U/μl | 50.00 | 0.33 | 0.13 | 112.3 |
| | | | Total Volume Mix (μl) | 7.43 | |

D Protocol synthesis cDNA

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A Mix C

| | | | | Reaction Vol. (μl) 25 | |
|---|---|---|---|---|---|
| Samples 833 | | | | Volume for (μl) | |
| | | Concentration | | | x |
| Mix Item | Unit | Stock | Final | 1 sample | samples |
| H$_2$O PCR grade Roche | | | | 7.74 | 6447.42 |
| Roche 2xMM mix | X | 2 | 1 | 12.50 | 10412.50 |
| F3utr258 | μM | 20 | 0.3 | 0.38 | 316.54 |
| R3utr425 | μM | 20 | 0.3 | 0.38 | 316.54 |
| P3utr343 | μM | 20 | 0.1 | 0.13 | 108.29 |
| Factin743 | μM | 20 | 0.3 | 0.38 | 316.54 |
| Ractin876 | μM | 20 | 0.3 | 0.38 | 316.54 |
| Pactin773 | μM | 20 | 0.1 | 0.13 | 108.29 |
| | | | Volume Mix/Tube (μl) | 22.02 | |
| | | | cDNA | 3.00 | |

B Protocol qPCR3

| Step | Temp | Time | Ramp rate | |
|---|---|---|---|---|
| preincub/denat | 95° C. | 10 min | 4.4 | 40 cycles |
| Denaturation | 95° C. | 10 sec | 4.4 | |
| annealing | 58° C. | 1 min | 2.2 | |
| Elongation | 72° C. | 1 sec | 4.4 | |
| Cooling | 40° C. | 10 sec | 1.5 | |

Tetravalent Quantitative Reverse Transcriptase-PCR (RT-qPCR) Assay: Protocol B.

Vero cells (4×10$^4$) were seeded in 96-well plates. After one day, cell culture medium was replaced with 100 μL assay medium containing a 2×, 3× or 5× serial dilution of the compound (concentration range: 50 μg/mL-0.00038 μg/mL, 50 μg/mL-0.0076 μg/mL, and 50 μg/mL-0.00013 μg/mL, respectively) and 100 μL of dengue virus dilution, where a Ct of ~20 was achieved in RTqPCR. Following a 2 hour incubation period, the cell monolayer was washed 3 times with assay medium to remove residual, non-adsorbed virus and cultures were further incubated for either 4 days (DENV-2 NGC-Tongalike) or 7 days (DENV-1 Djibouti strain D1/H/IMTSSA/98/606, DENV-3 strain H87 prototype, DENV-4 strain H241') in the presence of the inhibitor. Supernatant was harvested and viral RNA load was determined by real-time quantitative RT-PCR. The 50% effective concentration ($EC_{50}$), which is defined as the compound concentration that is required to inhibit viral RNA replication by 50%, was determined using logarithmic interpolation (Tables 7 and 8). RNA was isolated from 100 μL supernatant with the NucleoSpin 96 Virus kit (Filter Service, Duren, Germany) as described by the manufacturer. The sequences of the TaqMan primers (DENV-For, DENV-Rev; Table 5) and TaqMan probes (DENV-Probe Table 5) were selected from non-structural gene 3 (NS3) or NS5, of the respective flaviviruses using Primer Express software (version 2.0; Applied Biosystems, Lennik, Belgium). The TaqMan probe was fluorescently labelled with 6-carboxyfluorescein (FAM) at the 5' end as the reporter dye, and with minor groove binder (MGB) at the 3' end as the quencher (Table 5). One-step, quantitative RT-PCR was performed in a total volume of 25 μL, containing 13.9375 μL H$_2$O, 6.25 μL master mix (Eurogentec, Seraing, Belgium), 0.375 μL forward primer, 0.375 μL reverse primer, 1 μL probe, 0.0625 μL reverse transcriptase (Eurogentec) and 3 μL sample. RT- PCR was performed using the ABI 7500 Fast Real-Time PCR System (Applied Biosystems, Branchburg, N.J., USA) using the following conditions: 30 min at 48° C. and 10 min at 95° C., followed by 40 cycles of 15 s at 95° C. and 1 min at 60° C. The data was analyzed using the ABI PRISM 7500 SDS software (version 1.3.1; Applied Biosystems). For absolute quantification, standard curves were generated using 10-fold dilutions of template preparations of known concentrations.

TABLE 5

Primers and probes used for real-time, quantitative RT-PCR.

| Primer/Probe | Sequence (5'→3') [a] | Source [b] | Target |
|---|---|---|---|
| DENV-For | TCGGAGCCGGAGTTTACAAA (SEQ ID N. 7) | DENV 2 NGC | NS3 |
| DENV-Rev | TCTTAACGTCCGCCCATGAT (SEQ ID N. 8) | | |
| DENV-Probe | FAM-ATTCCACACAATGTGGC AT-MGB (SEQ ID N. 9) | | |
| DenS | GGATAGACCAGAGATCCTGCT GT (SEQ ID N. 10) | DENV-1, -3, -4 | NS5 |
| DenAS1-3 | CATTCCATTTTCTGGCGTTC (SEQ ID N. 11) | DENV-1, -3 | |
| DenAS4 | CAATCCATCTTGCGGCGCTC (SEQ ID N. 12) | DENV-4 | |
| DEN_1-3 probe | FAM-CAGCATCATTCCAGGCAC AG-MGB (SEQ ID N. 13) | DENV-1, -3 | |
| DEN_4 probe | FAM-CAACATCAATCCAGGCAC AG-MGB (SEQ ID N. 14) | DENV-4 | |

[a] Reporter dye (FAM) and quencher (MGB/TAMRA) elements are indicated in bold and italics.
[b] The nucleotide sequence and position of the primers and probes within the genome were deduced from the nucleotide sequence of DENV 2 NGC (GenBank accession no. M29095; Irie et al., 1989), dengue virus serotype 1 Djibouti strain D1/H/IMTSSA/98/606 (Genbank Accession Number AF298808), dengue virus serotype 3 strain H87 prototype (c93130), dengue virus serotype 4 strain H241 (no sequences available).

Cytotoxic Assay (Protocol B)

Potential cytotoxic effects of the compounds were evaluated in uninfected Vero cells. Cells were seeded at $4 \times 10^4$ cells/well in a 96-well plate in the presence of two-, three- or five-fold serial dilutions (ranging from 50 µg/mL-0.0038 µg/mL, 50 µg/mL-0.0076 µg/mL, and 50 µg/mL-0.00013 µg/mL, respectively) of compound and incubated for 4 to 7 days. Culture medium was discarded and 100 µL 3-(4,5-dimethylthiazol-2-yl)-5-(3-carboxymethoxyphenyl)-2-(4-sulfophenyl)-2H-tetrazolium/phenazinemethosulfate (MTS/PMS; Promega, Leiden, The Netherlands) in PBS was added to each well. Following a 2-hour incubation period at 37° C., the optical density was determined at 498 nm. Cytotoxic activity was calculated using the following formula: % cell viability=$100 \times (OD_{Compound}/OD_{CC})$, where $OD_{compound}$ and $OD_{CC}$ correspond to the optical density at 498 nm of the uninfected cell cultures treated with compound and that of uninfected, untreated cell cultures, respectively. The 50% cytotoxic concentration (i.e., the concentration that reduces the total cell number with 50%; $CC_{50}$) was calculated using linear interpolation (Tables 7 and 8).

TABLE 6

$EC_{50}$, $CC_{50}$, and SI for the compounds against serotype 1 in the RT-qPCR assays Protocol A
RT-qPCR serotype 1 TC974#666

| compound# | EC50 (µM) | N | CC50 (µM) | N | SI | N |
|---|---|---|---|---|---|---|
| 1A | 0.018 | 6 | 8.7 | 5 | 447 | 5 |
| 2B | 0.013 | 3 | 3.6 | 3 | 261 | 3 |
| 3A | 0.016 | 3 | 4.1 | 3 | 224 | 3 |
| 4A | 0.020 | 3 | 5.9 | 3 | 280 | 3 |
| 5B | 0.027 | 3 | 6.3 | 3 | 224 | 3 |
| 6A | 0.016 | 3 | 5.4 | 3 | 327 | 3 |
| 7A | 0.029 | 3 | 3.8 | 3 | 129 | 3 |
| 8A | 0.032 | 3 | 10 | 3 | 291 | 3 |
| 9B | 0.019 | 3 | 3.8 | 3 | 175 | 3 |
| 10B | 0.016 | 3 | 3.8 | 3 | 261 | 3 |
| 11A | 0.020 | 3 | 6.3 | 2 | 307 | 2 |
| 12B | 0.020 | 3 | 5.0 | 3 | 230 | 3 |

Protocol B
RT-qPCR serotype 1 Djibouti

| compound# | EC50 (µM) | N | CC50 (µM) | N | SI | N |
|---|---|---|---|---|---|---|
| 1A | 0.040 | 3 | 13 | 5 | 333 | 2 |
| 2B | 0.041 | 3 | 9.2 | 6 | 265 | 3 |
| 3A | 0.045 | 3 | 7.6 | 6 | 144 | 2 |
| 4A | 0.027 | 3 | 9.7 | 6 | 325 | 2 |
| 5B | 0.065 | 3 | 12 | 7 | 172 | 3 |
| 6A | 0.021 | 3 | 9.7 | 9 | 341 | 3 |
| 7A | 0.055 | 3 | 16 | 5 | 308 | 2 |
| 8A | 0.049 | 3 | 9.6 | 8 | 206 | 3 |
| 9B | 0.042 | 3 | 8.8 | 6 | 263 | 3 |
| 10B | 0.052 | 2 | 7.3 | 5 | 141 | 2 |
| 11A | 0.023 | 2 | 11 | 5 | 534 | 2 |
| 12B | 0.096 | 3 | 9.4 | 8 | 97 | 3 |

N = the number of independent experiments in which the compounds were tested.

TABLE 7

$EC_{50}$, $CC_{50}$, and SI for the compounds against serotype 2 in the RT-qPCR assays Protocol A
RT-qPCR serotype 2 16681

| compound# | EC50 (µM) | N | CC50 (µM) | N | SI | N |
|---|---|---|---|---|---|---|
| 1A | 0.0032 | 6 | 12 | 6 | 4043 | 6 |
| 2B | 0.0023 | 3 | 4.9 | 3 | 1700 | 3 |
| 3A | 0.00079 | 4 | 4.2 | 4 | 5745 | 4 |
| 4A | 0.0016 | 3 | 13 | 3 | 7510 | 3 |
| 5B | 0.0036 | 3 | 3.6 | 3 | 1087 | 3 |
| 6A | 0.0017 | 6 | 4.1 | 6 | 2535 | 6 |
| 7A | 0.0034 | 4 | 4.3 | 4 | 1316 | 4 |
| 8A | 0.00090 | 4 | 10 | 4 | 11745 | 4 |
| 9B | 0.0032 | 4 | 3.7 | 4 | 1180 | 4 |
| 10B | 0.0032 | 3 | 6.5 | 3 | 1818 | 3 |
| 11A | 0.00084 | 5 | 7.2 | 6 | 9329 | 5 |
| 12B | 0.0081 | 3 | 4.7 | 3 | 520 | 3 |

Protocol B
RT-qPCR serotype 2 NGC-Tongalike

| compound# | EC50 (µM) | N | CC50 (µM) | N | SI | N |
|---|---|---|---|---|---|---|
| 1A | 0.0010 | 3 | 13 | 3 | 11200 | 1 |
| 2B | 0.00081 | 3 | 15 | 3 | 18500 | 3 |
| 3A | <0.00028 | 5 | 13 | 4 | 46900 | 4 |
| 4A | <0.00029 | 3 | 18 | 3 | 109414 | 1 |
| 5B | 0.00044 | 3 | 11 | 3 | 30000 | 1 |

TABLE 7-continued

EC$_{50}$, CC$_{50}$, and SI for the compounds against serotype 2 in the RT-qPCR assays

| 6A | <0.00035 | 5 | 17 | 3 | 39200 | 3 |
|---|---|---|---|---|---|---|
| 7A | 0.0016 | 3 | 18 | 3 | 9980 | 1 |
| 8A | <0.00024 | 4 | NA |  | NA |  |
| 9B | 0.00080 | 2 | 14 | 2 | 17500 | 2 |
| 10B | 0.0016 | 3 | 11 | 3 | 6750 | 3 |
| 11A | 0.00068 | 3 | 12 | 3 | 17600 | 1 |
| 12B | 0.0017 | 3 | 14 | 3 | 8070 | 3 |

N = the number of independent experiments in which the compounds were tested.
NA: not approved.

TABLE 8

EC$_{50}$, CC$_{50}$, and SI for the compounds against serotype 3 in the RT-qPCR assays

| Protocol A RT-qPCR serotype 3 H87 | | | | | |
|---|---|---|---|---|---|
| compound# | EC50 (μM) | N | CC50 (μM) | N | SI | N |
| 1A | 0.12 | 6 | 4.4 | 5 | 38 | 5 |
| 2B | 0.11 | 3 | >2.5 | 1 | >32 | 1 |
| 3A | 0.088 | 3 | 2.2 | 2 | 23 | 2 |
| 4A | 0.14 | 3 | 3.6 | 3 | 22 | 3 |
| 5B | 0.19 | 3 | 3.4 | 3 | 20 | 3 |
| 6A | 0.13 | 3 | 3.1 | 2 | 27 | 2 |
| 7A | 0.19 | 3 | 3.9 | 2 | 24 | 2 |
| 8A | 0.20 | 3 | 5.8 | 2 | 41 | 2 |
| 9B | 0.19 | 3 | >2.5 | 1 | >12 | 1 |
| 10B | 0.13 | 3 | 2.3 | 3 | 18 | 3 |
| 11A | 0.085 | 3 | 3.7 | 3 | 44 | 3 |
| 12B | 0.27 | 3 | 2.8 | 3 | 11 | 3 |

| Protocol B RT-qPCR serotype 3 H87 | | | | | |
|---|---|---|---|---|---|
| compound# | EC50 (μM) | N | CC50 (μM) | N | SI | N |
| 1A | 0.053 | 3 | 13 | 5 | 207 | 3 |
| 2B | 0.042 | 3 | 9.2 | 6 | 188 | 1 |
| 3A | 0.032 | 4 | 7.6 | 6 | 232 | 4 |
| 4A | 0.016 | 3 | 9.7 | 6 | 443 | 3 |
| 5B | 0.050 | 3 | 12 | 7 | 212 | 3 |
| 6A | 0.020 | 5 | 9.7 | 9 | 484 | 4 |
| 7A | 0.041 | 3 | 16 | 5 | 339 | 3 |
| 8A | 0.029 | 5 | 9.6 | 8 | 324 | 5 |
| 9B | 0.066 | 3 | 8.8 | 6 | 109 | 1 |

TABLE 8-continued

EC$_{50}$, CC$_{50}$, and SI for the compounds against serotype 3 in the RT-qPCR assays

| 10B | <0.022 | 3 | 7.3 | 5 | >337 | 3 |
|---|---|---|---|---|---|---|
| 11A | 0.040 | 3 | 11 | 5 | 261 | 3 |
| 12B | 0.077 | 4 | 9.4 | 8 | 133 | 4 |

N = the number of independent experiments in which the compounds were tested.

TABLE 9

EC$_{50}$, CC$_{50}$, and SI for the compounds against serotype 4 in the RT-qPCR assays.

| Protocol A RT-qPCR serotype 4 H241 | | | | | |
|---|---|---|---|---|---|
| compound# | EC50 (μM) | N | CC50 (μM) | N | SI | N |
| 1A | 0.48 | 6 | 9.0 | 7 | 16 | 6 |
| 2B | 0.32 | 3 | 3.7 | 3 | 11 | 3 |
| 3A | 0.24 | 5 | 2.8 | 4 | 12 | 4 |
| 4A | 0.40 | 4 | 7.0 | 4 | 17 | 4 |
| 5B | 0.45 | 3 | 2.5 | 3 | 5 | 3 |
| 6A | 0.20 | 6 | 2.8 | 6 | 15 | 6 |
| 7A | 0.47 | 4 | 2.4 | 3 | 4 | 3 |
| 8A | 0.52 | 4 | 6.6 | 3 | 15 | 3 |
| 9B | 0.39 | 4 | 2.9 | 4 | 7 | 4 |
| 10B | 0.39 | 3 | 4.5 | 2 | 7 | 2 |
| 11A | 0.35 | 5 | 5.1 | 4 | 15 | 4 |
| 12B | 0.29 | 3 | 5.0 | 3 | 20 | 3 |

| Protocol A RT-qPCR serotype 4 EDEN | | | | | |
|---|---|---|---|---|---|
| compound# | EC50 (μM) | N | CC50 (μM) | N | SI | N |
| 1A | 0.012 | 6 | 12 | 6 | 1066 | 6 |
| 2B | 0.011 | 4 | 4.9 | 4 | 416 | 4 |
| 3A | 0.016 | 4 | 4.1 | 3 | 261 | 3 |
| 4A | 0.016 | 4 | 6.7 | 4 | 422 | 4 |
| 5B | 0.024 | 4 | 5.6 | 4 | 223 | 4 |
| 6A | 0.013 | 4 | 6.6 | 4 | 506 | 4 |
| 7A | 0.023 | 4 | 4.5 | 4 | 184 | 4 |
| 8A | 0.021 | 4 | 6.8 | 4 | 311 | 4 |
| 9B | 0.020 | 4 | 4.9 | 4 | 236 | 4 |
| 10B | 0.020 | 4 | 6.0 | 4 | 284 | 4 |
| 11A | 0.015 | 5 | 4.8 | 3 | 235 | 3 |
| 12B | 0.017 | 3 | 3.8 | 3 | 219 | 3 |

N = the number of independent experiments in which the compounds were tested.

The invention claimed is:

1. A compound of formula (I)

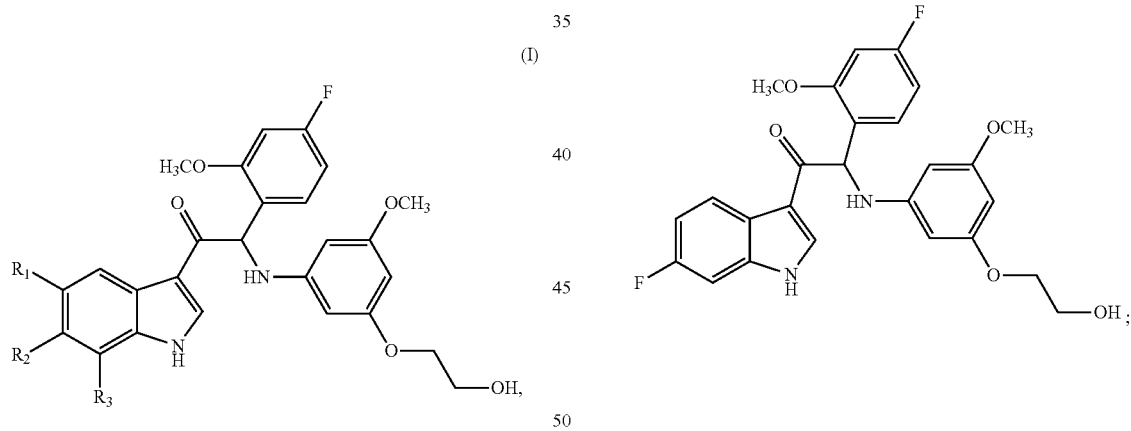

wherein:

(1) $R_1$ is H, $R_2$ is F, and $R_3$ is H, F or $CH_3$;

(2) $R_1$ is F or $CH_3$, $R_2$ is $OCH_3$, and $R_3$ is H;

(3) $R_1$ is H, $R_2$ is Cl, and $R_3$ is H or $CH_3$;

(4) $R_1$ is F, $R_2$ is H, and $R_3$ is $CH_3$;

(5) $R_1$ is H, $R_2$ is $OCH_3$, and $R_3$ is Cl;

(6) $R_1$ is F, $R_2$ is F, and $R_3$ is H;

(7) $R_1$ is H, $R_2$ is $OCH_3$, and $R_3$ is $CH_3$; or (8) $R_1$ is $CH_3$, $R_2$ is H, and $R_3$ is F;

or a stereo-isomeric form, a pharmaceutically acceptable salt, solvate or polymorph thereof.

2. A compound selected from the group consisting of:

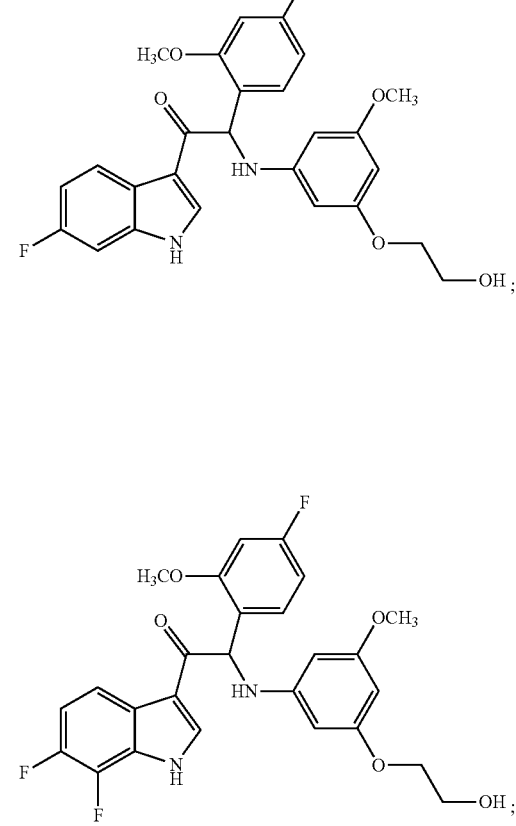

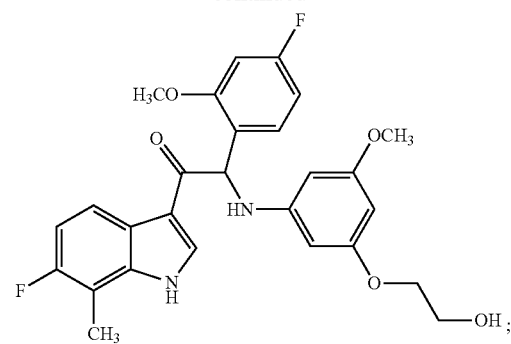
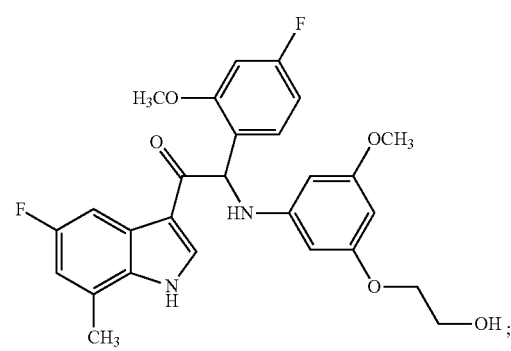
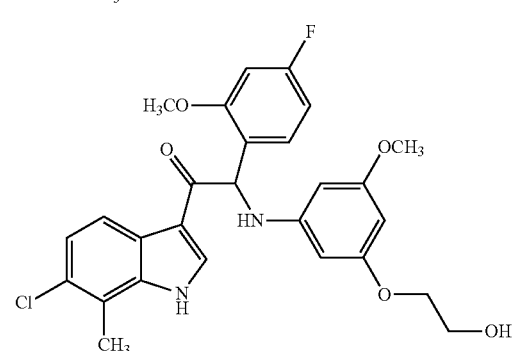
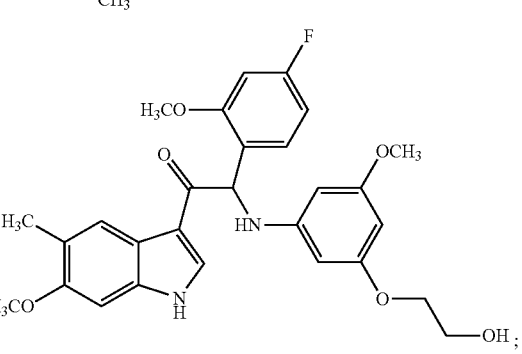
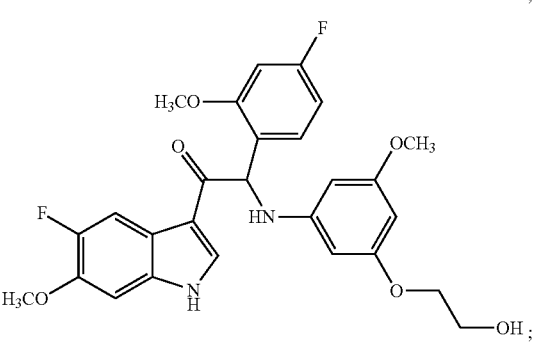

-continued

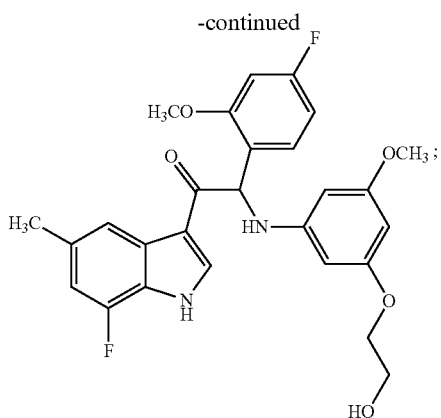

or a stereo-isomeric form, a pharmaceutically acceptable salt, solvate or polymorph thereof.

3. A pharmaceutical composition comprising a compound of formula (I) or a stereo-isomeric form, a pharmaceutically acceptable salt, solvate or polymorph thereof, according to claim 1 and one or more pharmaceutically acceptable excipients, diluents or carriers.

4. A method of treating a dengue viral infection, comprising administering a therapeutically effective amount of at least one compound or a stereo-isomeric form, a pharmaceutically acceptable salt, solvate or polymorph thereof as claimed in claim 1 to a patient in need thereof.

5. A method of inhibiting the replication of dengue virus in a biological sample or patient, comprising administering a therapeutically effective amount of at least one compound or a stereo-isomeric form, a pharmaceutically acceptable salt, solvate or polymorph thereof as claimed in claim 1 to said biological sample or patient in need thereof.

6. The method as claimed in claim 5 further comprising co-administering an additional therapeutic agent.

7. The method as claimed in claim 6, wherein said additional therapeutic agent is another antiviral agent.

8. A pharmaceutical composition comprising a compound or a stereo-isomeric form, a pharmaceutically acceptable salt, solvate or polymorph thereof according to claim 2 and one or more pharmaceutically acceptable excipients, diluents or carriers.

9. A method of treating a dengue viral infection, comprising administering a therapeutically effective amount of at least one compound or a stereo-isomeric form, a pharmaceutically acceptable salt, solvate or polymorph thereof as claimed in claim 2 to a patient in need thereof.

* * * * *